(12) United States Patent
Omori et al.

(10) Patent No.: US 8,012,731 B2
(45) Date of Patent: Sep. 6, 2011

(54) PHOSPHODIESTERASE AND GENE THEREOF

(75) Inventors: Kenji Omori, Saitama (JP); Keizo Yuasa, Toda (JP); Jun Kotera, Hasuda (JP); Kotomi Oda, Himeji (JP); Hideo Michibata, Takatsuki (JP)

(73) Assignee: Tanabe Seiyaku Co., Ltd., Osaka (JP)

( * ) Notice: Subject to any disclaimer, the term of this patent is extended or adjusted under 35 U.S.C. 154(b) by 704 days.

(21) Appl. No.: 11/960,999

(22) Filed: Dec. 20, 2007

(65) Prior Publication Data

US 2009/0325207 A1    Dec. 31, 2009

Related U.S. Application Data

(62) Division of application No. 10/168,402, filed as application No. PCT/JP00/09118 on Dec. 22, 2000, now Pat. No. 7,332,317.

(30) Foreign Application Priority Data

Dec. 22, 1999  (JP) ................................. 11-364866
Jun. 1, 2000   (JP) ................................. 2000-163875

(51) Int. Cl.
| | |
|---|---|
| C07H 21/00 | (2006.01) |
| C12N 15/00 | (2006.01) |
| C12Q 1/68 | (2006.01) |
| C12N 1/21 | (2006.01) |
| C12N 5/10 | (2006.01) |
| C12N 9/16 | (2006.01) |
| C12P 21/00 | (2006.01) |

(52) U.S. Cl. ................... 435/196; 435/320.1; 435/69.1; 435/325; 435/252.3; 435/6; 536/23.2

(58) Field of Classification Search ................. 435/196, 435/320.1, 69.1, 325, 252.3, 18; 536/23.2; 530/350
See application file for complete search history.

(56) References Cited

U.S. PATENT DOCUMENTS 6,100,037 A * 8/2000 Phillips et al. ............ 506/9

FOREIGN PATENT DOCUMENTS

EP    1 211 313 A2    6/2002

OTHER PUBLICATIONS

Stacey et al., Biochemical and Biophysical Research Communications 247:249-254, Jun. 1998.*
Branden et al., Introduction to Protein Structure, Garland Publishing Inc., New York, p. 247, 1991.*
Seffernick et al., J. Bacteriol. 183(8):2405-2410, 2001.*
Witkowski et al., Biochemistry 38:11643-11650, 1999.*
Houdebine, L., Journal of Biotechnology 98:145-160, 2002.*
Phillips, A., J. Pharm. Pharmacology 53:1169-1174, 2001.*
Gardlik et al., Med. Sci. Monit. 11(4):RA110-121, 2005.*
Cameron, E., Molecular Biotechnology 7:253-265, 1997.*
Kappel et al., Current Opinion in Biotechnology 3:548-553, 1992.*
Mullins et al., Hypertension 22(4):630-633, 1993.*
Mullins et al., J. Clin. Invest. 97(7):1557-1560, 1996.*
Noriyuki Yanaka et al; "Expression, structure and chromosomal localization of the human cGMP-binding cGMP-specific phosphodiesterase PDE5A gene;" Eur. J. Biochem (1998); vol. 255, No. 2, pp. 391-399.
Linda McAllister-Lucas et al; "The Structure of a Bovine Lung cGMP-binding, cGMP-specific Phosphodiesterase Deduced from a cDNA Clone;" Journal of Biological Chemistry; 1993, vol. 268, No. 30; pp. 22863-22873.
Lindsay Fawcett et al; "Molecular cloning and characterization of a distinct human phosphodiesterase gene family: PDE11A;" Proc. Natl. Acad. Sci. USA; Mar. 2000, vol. 97, No. 7, pp. 3702-3707.
Kotomi Fujishige et al; "Cloning and Characterization of a Novel Human Phosphodiesterase That Hydrolyzes Both camp and cGMP (PDE10A);" Journal of Biological Chemistry; 1999, vol. 274, No. 26, pp. 18438-18445.
Keizo Yuasa, et al; "Isolation and Characterization of Two Novel Phosphodiesterase PDE11A Variants Showing Unique Structure and Tissue-specific Expression;" Journal of Biological Chemistry; Oct. 2000, vol. 275, No. 40, pp. 31469-31479.
Guy Rosman et al; "Isolation and characterization of human cDNAs encoding a cGMP-stimulated 3", 5A-cyclic nucleotide phosphodiesterase;" Gene, 1997, vol. 191, pp. 89-95.
J.M. Hetman et al., "Cloning and Characterization of Two Splice Variants of Human Phosphodiesterase 11A", Proc. Natl. Acad. Sci., vol. 97, pp. 12891-12895 (2000).
K. Yuasa et al., "Genomic Organization of the Human Phosphodiesterase PDE11A Gene", Eur. J. Biochem., vol. 268, pp. 168-178 (2001).
K. Yuasa et al., "Identification of Rat Cyclic Nucleotide Phosphodiesterase 11A (PDE11A)", Eur. J. Biochem., vol. 268, pp. 4440-4448 (2001).
Gen Bank ID No:AI 025081, Aug. 13, 1998.
Wong et al., PNAS, 103:(41)15124-15129 (Oct. 10, 2006).

* cited by examiner

Primary Examiner — Delia Ramirez
(74) Attorney, Agent, or Firm — Browdy and Neimark PLLC

(57) ABSTRACT

The present invention is to provide a novel phosphodiesterase and a gene thereof, specifically, Type 11 phosphodiesterase (PDE11) and a gene thereof, more specifically, a phosphodiesterase selected from (A) a protein having an amino acid sequenced shown by SEQ.ID.NO: 2, SEQ.ID.NO: 4, SEQ.ID.NO: 6 or SEQ.ID.NO: 39, and (B) a protein having an amino acid sequence shown by SEQ.ID.NO: 2, SEQ.ID.NO: 4, SEQ.ID.NO: 6 or SEQ.ID.NO: 39 in which one or several amino acids are deleted, substituted or added, and having an activity of hydrolyzing a cyclic nucleotide, and a gene thereof, and a method of characterizing, identifying and selecting a phosphodiesterase inhibitor by using the same.

9 Claims, 3 Drawing Sheets

—○— ; cGMP hydrolysis reaction
—●— ; cAMP hydrolysis reaction

—△— ; cGMP hydrolysis reaction
—▲— ; cAMP hydrolysis reaction

———●——— ; cGMP hydrolysis reaction by humanPDE11A1

———○——— ; cAMP hydrolysis reaction by humanPDE11A1

———▲——— ; cGMP hydrolysis reaction by humanPDE11A2

———△——— ; cAMP hydrolysis reaction by humanPDE11A2

Fig. 4

| | | | | | | | | | | |
|---|---|---|---|---|---|---|---|---|---|---|
| Total Brain | Cerebellum (Left) | Substantia Nigra | Heart | Esophagus | Transverse Colon | Kidney | Lung | Liver | Leukemia Cell HL-60 | Fetal Brain |
| Cerebral Cortex | Cerebellum (Right) | Accumbens Nucleus | Aorta | Stomach | Descending Colon | Skeletal Muscle | Placenta | Pancreas | HeLa Cell S3 | Fetal Heart |
| Frontal Lobe | Corpus Callosum | Thalamus | Left Atrium | Duodenum | Rectum | Spleen | Bladder | Adrenal Gland | Leukemia Cell K-562 | Fetal Kidney |
| Parietal Lobe | Amygdala | Pituitary Gland | Right Atrium | Jejunum | | Thymus | Uterus | Thyroid Gland | Leukemia Cell MOLT-4 | Fetal Liver |
| Occipital Lobe | Caudate Nucleus | Spinal Cord | Left Ventricle | Ileum | | Peripheral Blood Leukocyte | Prostate | Salivary Gland | Burkitt Lymphoma Cell Raji | Fetal Spleen |
| Temporal Lobe | Hippocampus | | Right Ventricle | Ileocecum | | Lymph Node | Testis | Mammary Gland | Burkitt Lymphoma Cell Daudi | Fetal Thymus |
| Cerebral Cortex Paracentral Gyrus | Medulla Oblongata | | Interventricular Septum | Appendix Vermiformis | | Bone Marrow | Ovary | | Colorectal Adenocarcinoma Cell Sw480 | Fetal Lung |
| Pons | Putamen | | Apex of the Heart | Ascending Colon | | Trachea | | | Lung Carcinoma Cell A549 | |

PHOSPHODIESTERASE AND GENE THEREOF

CROSS-REFERENCE TO RELATED APPLICATIONS

The present application is a divisional of application Ser. No. 10/168,402 filed Jun. 21, 2002, now issued as U.S. Pat. No. 7,332,317, which is a 371 national stage of PCT/JP00/09118, filed Dec. 22, 2000, which claims priority from JP 364866/1999, filed Dec. 22, 1999, and JP 163875/2000, filed Jun. 1, 2000. The entire contents of prior applications are herein incorporated by reference.

TECHNICAL FIELD

The present invention relates to a novel phosphodiesterase and its gene.

BACKGROUND ART

Cyclic nucleotide such as cAMP, cGMP, etc. are involved in regulations of many in vivo functions as the second messenger in the intracellular signal transduction (Kukovetz et al., Naunyn Schmiedeberg's Arch. Pharmacol., Vol. 310, pp. 129-138, 1979; Schram et al., Science, Vol. 225, pp. 1350-1356, 1984; Ignarro et al., Annu. Rev. Pharmacol. Toxicol., Vol. 25, pp. 171-191, 1985; Martin et al., J. Pharmacol. Exp., Vol. 237, pp. 539-547, 1986).

Intracellular concentrations of the cAMP and cGMP, changing in response to an extracellular signal, are regulated by a balance between adenylcyclase and guanylcyclase involved in a synthesis thereof, and phosphodiesterase (PDE) involved in a hydrolysis of cyclic nucleotides.

Until recently, many phosphodiesterases have been found from tissues of mammals which hydrolyze cyclic nucleotides, and they have been classified into plural types, according to homology of amino acid sequence, biochemical properties, characterization by an inhibitor, etc. (Beavo, Physiol.Rev., Vol 75, pp. 725-748, 1995).

For example, PDE1 is $Ca^{2+}$/calmodulin dependent PDE and hydrolyses both cAMP and cGMP. PDE2 is activated by cGMP and hydrolyses both cAMP and cGMP. PDE classified as PDE3 is inhibited by cGMP. PDE4 specifically recognizes cAMP as a substrate, and is Rolipram-sensitive. PDE5 specifically recognizes cGMP as a substrate. PDE6 is a photoreceptor cGMP-PDF. PDE7 specifically recognizes cAMP as a substrate, and is not sensitive to Rolipram.

Further recently, existences of 3 kinds of novel types of PDE have been reported. One is called PDE8, specifically recognizing cAMP as a substrate, and another is called PDE9, specifically recognizing cGMP as a substrate (Soderling et al., Proc. Natl. Acad. Sci. USA, Vol. 95, pp. 8991-8996, 1998; Fisher et al., Biochem. Biophys. Res. Commun., Vol. 246, pp. 570-577, 1998; Soderling et al., J. Biol. Chem., Vol. 273, pp.15553-15558, 1998; Fisher et al., J. Biol. Chem., Vol. 273, pp. 15559-15564, 1998; Hayashi et al., Biochem. Biophys. Res. Commun., Vol. 250, pp. 751-756, 1998). These two PDEs are reported to be insensitive to IBMX (3-isobutyl-1-methylxanthine). Still another one is called PDE10, recognizing both cAMP and cGMP as a substrate. However, it has been reported to show stronger affinity toward cAMP (Fujishige et al., J. Biol. Chem., Vol. 274, pp. 18438-18445, 1999; Kotera et al., Biochem. Biophys. Res. Commun., Vol., 261, pp. 551-557, 1999).

Also, PDE is an important target compound for research and development in a pharmaceutical field, and research on its inhibitor has been earnestly carried out. Among the known pharmaceuticals, there have been found those having an inhibitory action on PDE, and also, it has been found that a specific PDE inhibitor can serve as a useful therapeutic agent.

For example, Milrinone and Zaprinast as a cardiac are inhibitors of PDE3 and PDE5, respectively (Harrison et al., Mol. Pharmacol., Vol. 29, pp. 506-514, 1986; Gillespie et al., Mol. Pharmacol., Vol. 36, pp. 773-781, 1989). Also, Rolipram whose antidepressant activity has been reported is a PDE4 inhibitor (Schneider et al., Eur. J. Pharmacol., Vol. 127, pp. 105-115, 1986). PDE4 inhibitor has been also developed and tested as an anti-inflammatory agent or an antasthmatic agent.

On top of that, IBMX is known as a non-selective type inhibitor acting on many types of PDEs. Vinpocetine is known to be a PDE1 inhibitor, EHNA [erythro-9-(2-hydroxy-3-nonyl)adenine] is known to be a PDE2 inhibitor, Dipyridamole is known to be an inhibitor of PDE5 and PDE6. Also, SCH51866 ((+)-cis-5-methyl-2-[4-(trifluoromethyl)benzyl]-3,4,5,6a,7,8,9,9a-octahydrocyclopent[4,5]imidazo-[2,1-b]purin-4-one; U.S. Pat. No. 5,939,419) is known to be an inhibitor of PDE1 and PDE5, and E4021 (sodium 1-[6-chloro-4-(3,4-methylenedioxybenzyl)aminoquinazolin-2-yl]pyperidine-4-carboxylate; CAS Registration No. 150452-19-0) is known to be an inhibitor of PDE5.

For development of an excellent pharmaceutical with a high therapeutic effect and less side effect, it is expected to choose an inhibitor having a high selectivity toward a certain type of PDE as a target.

Moreover, it has been sought to find a novel type of PDE, being a different molecular species from the known ones, for studying a complex mechanism of intracellular signal transduction, and also, for a possibility to become a target molecule of a new therapeutic agent.

An object of the present invention is to provide a novel type of phosphodiesterase [Type 11 phosphodiesterase (PDE11)] and its gene. Also, it is to provide a novel method for characterizing, identifying or selecting a phosphodiesterase inhibitor. Further, other objects than the above will be clear from the following descriptions.

DISCLOSURE OF THE INVENTION

The present inventors have isolated from human and rat a full-length cDNA which encodes a novel type of phosphodiesterase (also referred to as PDE11 or PDE11A.) which is a different molecular species from the known ones. Also, they have succeeded in expressing human phosphodiesterase (also referred to as PDE11 or PDE11A.) in COS cells by a genetic recombination technique and isolating the same. Moreover, they have characterized the enzymatic properties, whereby the present invention has completed.

That is, the present invention is Type 11 phosphodiesterase (PDE11) and its gene. More specifically, it is phosphodiesterase selected from the following (A) and (B), and a gene or a nucleic acid which encodes said phosphodiesterase.

(A) a protein having an amino acid sequence shown by SEQ.ID.NO: 2, SEQ.ID.NO: 4, SEQ.ID.NO: 6 or SEQ.ID.NO: 39, and (B) a protein having an amino acid sequence shown by SEQ.ID.NO: 2, SEQ.ID.NO: 4, SEQ.ID.NO: 6 or SEQ.ID.NO: 39 in which one or several amino acids are deleted, substituted or added, which has an activity of hydrolyzing a cyclic nucleotide.

As the gene or the nucleic acid which encodes the phosphodiesterase of the present invention, there may be mentioned a gene or a nucleic acid selected from the following (a) and (b):

(a) a gene or a nucleic acid comprising a DNA having a nucleotide sequence shown by SEQ.ID.NO: 1, SEQ.ID.NO: 3, SEQ.ID.NO: 5 or SEQ.ID.NO: 38, and (b) a gene or a nucleic acid comprising a DNA which hybridizes with a DNA having a nucleotide sequence shown by SEQ.ID.NO: 1, SEQ.ID.NO: 3, SEQ.ID.NO: 5 or SEQ.ID.NO: 38 under a stringent condition, and which encodes a protein having an activity of hydrolyzing a cyclic nucleotide.

Moreover, the present invention is a recombinant vector and a host cell containing said gene or said nucleic acid. Moreover, it is a method for characterizing, identifying or selecting a phosphodiesterase inhibitor using the same.

SEQ.ID.NO: 1 of the sequence listing mentioned below represents a nucleotide sequence of a cDNA containing an entire coding region of a human homologue (human PDE11 gene. Specifically, it is also referred to as a human PDE11A gene.) of the novel PDE gene isolated by the present inventors, and SEQ.ID.NO: 2 represents an amino acid sequence of the novel PDE (human PDE11. Specifically, it is also referred to as a human PDE11A1.) encoded by said full-length cDNA.

SEQ.ID.NO: 3 of the sequence listing mentioned below also represents a nucleotide sequence of a cDNA containing an entire coding region of a human homologue (human PDE11 gene. Specifically, it is also referred to as a human PDE11A gene.) of the novel PDE gene isolated by the present inventors, and SEQ.ID.NO: 4 represents an amino acid sequence of the novel PDE (human PDE11. Specifically, it is also referred to as a human PDE11A2.) encoded by said full-length cDNA.

SEQ.ID.NOs: 1 and 3 are nucleotide sequences of cDNAs of the two kinds of splicing variants of the human PDE11 gene, and SEQ.ID.NOs: 2 and 4 are amino acid sequences of PDE proteins of the each variant.

SEQ.ID.NO: 5 of the sequence listing mentioned below represents a nucleotide sequence of a cDNA containing an entire coding region of a rat homologue (rat PDE11 gene. Specifically, it is also referred to as a rat PDE11A gene.) of the novel PDE gene isolated by the present inventors, and SEQ.ID.NO: 6 represents an amino acid sequence of the novel PDE (rat PDE11. Specifically, it is also referred to as a rat PDE11A2.) encoded by said full-length cDNA.

SEQ.ID.NO: 38 of the sequence listing mentioned below also represents a nucleotide sequence of a cDNA containing an entire coding region of a rat homologue (rat PDE11 gene. Specifically, it is also referred to as a rat PDE11A gene.) of the novel PDE gene isolated by the present inventors, and SEQ.ID.NO: 39 represents an amino acid sequence of the novel PDE (rat PDE11. Specifically, it is also referred to as a rat PDE11A1.) encoded by said full-length cDNA SEQ.ID.NOs: 5 and 38 are nucleotide sequences of cDNAs of the two kinds of splicing variants of the rat PDE11 gene, and SEQ.ID.NOs: 6 and 39 are amino acid sequences of PDE proteins of the each variant.

As a result of homology search carried out with respect to the nucleotide sequences shown by the above-mentioned SEQ.ID.NOs: 1, 3, 5 and 38, and amino acid sequences shown by the above-mentioned SEQ.ID.NOs: 2, 4, 6 and 39, using known DNA data bases (GenBank and EMBL) and protein data bases (NBRF and SWISS-PROT), there was found nothing that is expected to be derived from the same kinds of molecular species, except for EST (Genbank/EMBL ID No:AI025081).

Moreover, as a result from a comparison between each of the amino acid sequences of the human PDE11 shown by SEQ.ID.NO: 4 and the rat PDE11 shown by SEQ.ID.NO: 6, a homology as high as about 93% was confirmed. Also, as a result from a comparison between each of the amino acid sequences of the human PDE11 shown by SEQ.ID.NO: 2 and the rat PDE11 shown by SEQ.ID.NO: 39, a homology as high as about 94% was confirmed.

BRIEF DESCRIPTION OF THE DRAWINGS

FIG. 4 shows kinds of organs and tissues of human for which an expression of the PDE11 gene was studied by dot blot analysis.

BEST MODE FOR CARRYING OUT THE INVENTION

Figure 1:
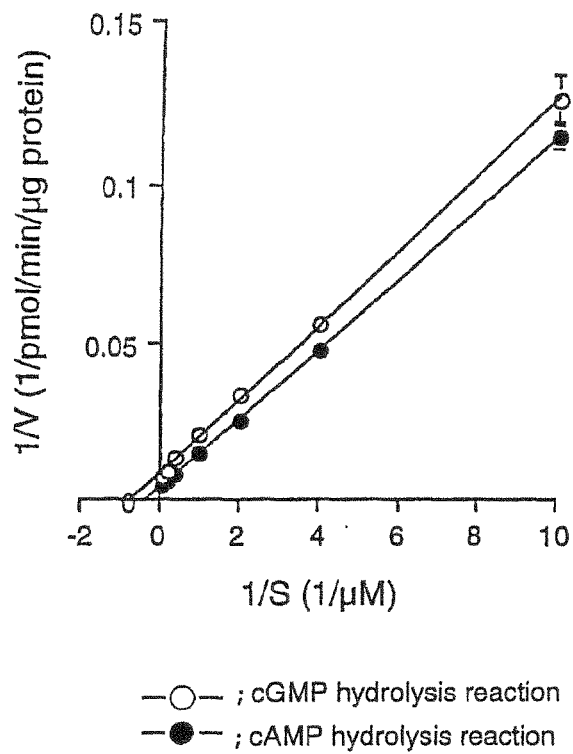
FIG. 1 shows a result of a kinetic analysis on hydrolysis of cAMP or cGMP by human PDE11A1 (Lineweaver-Burk plot).

As the protein of the present invention, there are mentioned those having an amino acid sequence shown by SEQ.ID.NO: 2, 4, 6 or 39. There are also mentioned those having an amino acid sequence shown by SEQ.ID.NO: 2, 4, 6 or 39, in which one or several amino acids are deleted, substituted or added.

Deletion, substitution and addition of the amino acids are admitted as long as the activity of hydrolyzing cyclic nucleotides is not lost, and normally, it is from 1 to about 420, preferably, from 1 to about 310, and more preferably, from 1 to about 165, further more preferably, from 1 to about 80, and still further preferably, from 1 to about 40.

As a region responsible for the activity of hydrolyzing cyclic nucleotides in PDE11 (PDE11A), that is, as a catalytic region of PDE11 (PDE11A), there are exemplified a region corresponding to from the $640^{th}$ to the $881^{st}$ amino acid residues of the amino acid sequence shown by SEQ.ID.NO: 2 of the below mentioned sequence listing, a region corresponding to from the $390^{th}$ to the $631^{st}$ amino acid residues of the amino acid sequence shown by SEQ.ID.NO: 4, etc.

In order not to loose the activity of PDE11 (PDE11A) for hydrolyzing cyclic nucleotides, it is expected that more amino acid sequences are conserved in a region responsible for the activity of the PDE11 (PDE11A), that is, in a catalytic region of the PDE11 (PDE11A) than in other regions.

Deletion, substitution or addition of the amino acids in the catalytic region of the PDE11 (PDE11A) is, normally from 1 to about 20, preferably from 1 to about 10, more preferably from 1 to about 5. Such a catalytic region of a protein has a homology with a catalytic region existing in the amino acid sequence shown in SEQ.ID.NO: 2 or 4, normally by about 90% or more, preferably about 95% or more, more preferably about 97% or more.

On the other hand, deletion, substitution or addition of the amino acids in a non-catalytic region of PDE11 (PDE11A) is normally from 1 to about 400, preferably from 1 to about 300, more preferably from 1 to about 160, further preferably from 1 to about 80, yet further preferably from 1 to about 40.

These proteins include an artificially modified mutant protein, a protein derived from other living species, etc., as well as naturally occurring mutant proteins.

As the gene or the nucleic acid of the present invention, there are mentioned those comprising a DNA having a nucleotide sequence shown by SEQ.ID.NO: 1, 3, 5 or 38. Also, there are mentioned those comprising a DNA which hybridizes with a DNA having a nucleotide sequence shown by SEQ.ID.NO: 1, 3, 5 or 38, under a stringent condition. There is no limitation for such a hybridizable DNA as long as it encodes a protein having an activity of hydrolyzing cyclic nucleotide. Such a DNA has a homology with a nucleotide sequence shown by SEQ.ID.NO: 1, 3, 5 or 38, by normally about 70% or more, preferably about 80% or more, more preferably about 90% or more. Such a gene or a nucleic acid includes an artificially modified mutant gene, a homologous gene derived from a different living species, etc., as well as a naturally occurring mutant gene.

In the present invention, hybridization under a stringent condition means carrying out hybridization, in case of a normal stringent conditions, in a hybridization solution of a salt concentration of 6×SSC or an equivalent thereof, at a temperature condition of 50~70° C. for 16 hours, optionally carrying out preliminary washing with a solution of a salt concentration of 6×SSC or an equivalent thereof, and washing in a solution of a salt concentration of 1×SSC or an equivalent thereof. Also, in case of a condition with a higher stringency (highly stringent condition), the above-mentioned washing is carried out in a solution of a salt concentration of 0.1×SSC or an equivalent thereof.

The gene or the nucleic acid of the present invention can be isolated by screening tissues or cells of mammals as a genetic source. As mammals, human as well as non-human animals such as dog, cow, horse, goat, sheep, ape, pig, rabbit, rat and mouse, etc. are mentioned. Among them, it is desirable to use one of human for a use in research and development of a therapeutic agent for human beings.

The gene or the nucleic acid of the present invention can be obtained by utilizing information on a sequence disclosed in the present specification (SEQ.ID.NO: 1, 3, 5 or 38 of the below mentioned sequence listing). For example, primers and probes are designed based on the information on the disclosed nucleotide sequence, and using the same, it can be chosen and obtained from the DNA library by suitably combining PCR (polymerase chain reaction) method, colony hybridization method and plaque hybridization method.

For example, cDNA is synthesized from mRNA prepared from cells or tissues of mammals, and using this as a template, cDNA fragment is obtained by PCR method. Using the obtained cDNA as a probe, cDNA library is screened by colony hybridization method or plaque hybridization method to obtain a full-length cDNA. Also, genomic DNA can be isolated by screening genomic DNA library. Further, by screening DNA library of other mammals, homologous genes from other living species can be isolated.

DNA library such as cDNA library, genomic DNA library, etc. can be prepared according to a method described in, for example, "Molecular Cloning" (written by Sambrook, J., Fritsch, E. F. and Maniatis, T., published by Cold Spring Harbor Laboratory Press in 1989). Alternatively, commercially available libraries can be used if they are available.

By determining a nucleotide sequence of the obtained cDNA, a coding region of the protein as a genetic product can be determined, thereby obtaining an amino acid sequence of this protein.

PDE of the present invention can be produced by overexpression by an usual recombinant DNA technique. Also, it can be produced in a form of a fusion protein with other protein or a peptide.

For example, a DNA coding PDE is inserted into a vector so that it is linked downstream of an appropriate promoter, thereby constructing an expression vector. Subsequently, the obtained expression vector is introduced in a host cell.

As an expression system (host-vector system), for example, expression systems such as bacteria, yeasts, insect cells and mammalian cells can be mentioned. Among these, for obtaining a functionally well preserved protein, insect cells (*Spodoptera frugiperda* SF9, SF21, etc.) and mammalian cells (monkey COS-7 cells, Chinese hamster CHO cells, human HeLa cells, etc.) are preferably used as a host.

As a vector, in case of the mammalian cell system, retrovirus type vector, papilloma virus vector, vaccinia virus vector, SV40 type vector, etc. can be used, and in case of the insect cell system, baculovirus vector, etc. can be used.

As a promoter, in case of the mammalian cell system, SV40 promoter, LTR promoter, elongation 1α promoter, etc., and in case of the insect cell system, polyhedrin promoter, etc, can be used.

As a DNA coding PDE, a cDNA corresponding to a naturally existing mRNA (for example, those comprising a nucleotide sequence shown by SEQ.ID.NO: 1, 3, 5 or 38) can be used, however, it is not limited to this. Alternatively, a DNA corresponding to an amino acid sequence of a desired protein is designed and used. In this case, 1 to 6 kinds are known for a codon coding each of an amino acid, and codons to be used may be chosen randomly. However, for example, by considering a codon usage (frequency) of a host to be used for expression, a sequence with a higher expression frequency can be designed. A DNA comprising the designed nucleotide sequence can be obtained by means of DNA chemical synthesis, fragmentation of the above cDNA and linking, partial modification of the nucleotide sequence, etc. Artificial and partial modification of the nucleotide sequence or an introduction of a mutation can be carried out by site specific mutagenesis (Proceedings of National Academy of Sciences, Vol. 81, pp. 5662 to 5666, 1984), etc., using a primer comprising a synthetic oligonucleotide coding a desired modification.

PDE of the present invention can be isolated and purified from a cultured product of the cells into which the expression vector is introduced, optionally combining known purification methods (salting out by inorganic salts, fractional precipitation, ion-exchange resin column chromatography, affinity column chromatography, gel filtration, etc.).

A nucleic acid (oligonucleotide or polynucleotide) which hybridizes with the gene or the nucleic acid of the present invention under a stringent condition can be used as a probe for detecting the gene of the present invention. Also, it can be used, for example, as an anti-sense oligonucleotide, a ribozyme, or a decoy for modifying an expression of a gene. As such a nucleic acid, for example, a nucleotide comprising a partial sequence of successive 14 bases or more, usually, in the nucleotide sequence shown by SEQ.ID.NO: 1, 3, 5 or 38, or a complementary sequence thereof can be used.

Using the PDE of the present invention or a protein or peptide having an immunological equivalency thereto (a synthetic peptide containing a fragment or a partial sequence of a protein) as an antigen, an antibody which recognizes the PDE of the present invention can be obtained. Immunological equivalency means, for example, ability to cross-react with an antibody against the PDE of the present invention.

A polyclonal antibody can be prepared by an ordinary method of inoculating a host animal (for example, rat, rabbit, etc.) with an antigen, and collecting immune serum. A monoclonal antibody can be prepared by an ordinary technique such as a hybridoma method. Further, a gene of a monoclonal antibody is modified to prepare a humanized monoclonal antibody.

Using the above-obtained antibody, an expression of PDE of the present invention in a cell or a tissue can be detected by an ordinary immunochemical method (enzyme immunoassay, etc.). Also, by means of an affinity chromatography using an antibody, purification of PDE of the present invention can be carried out.

The fact that PDE of the present invention has an activity of hydrolyzing a cyclic nucleotide (cAMP or cGMP) can be confirmed by a generally known method for measuring PDE activity (Thompson et al., Adv. Cyclic Nucleotide Res., Vol. 10, pp. 69-92, 1979; Yanaka et al., Eur. J. Biochem., Vol. 255, pp. 391-399, 1998).

As a substrate for an enzyme reaction, cyclic nucleotide such as cAMP, cGMP, etc. and their derivatives may be used. PDE of the present invention recognizes either of cAMP and cGMP as a substrate and hydrolyzes them.

PDE of the present invention can be used for characterization, identification or selection of phosphodiesterases inhibitors.

For example, by carrying out an enzyme reaction in a system containing PDE of the present invention, a substrate for the enzyme and a test substance (preferably a compound with a low molecular weight, etc.), an inhibitory action of the test substance on the enzyme activity (an activity of hydrolyzing a cyclic nucleotide) is determined.

Alternatively, by carrying out a binding reaction in a system containing PDE of the present invention and a test substance (preferably a compound with a low molecular weight, etc.), whether or not the test substance has a binding ability toward PDE of the present invention is determined. A test substance having a binding ability (a ligand) has a high possibility to serve as an inhibitor.

Moreover, by measuring an inhibitory action (or a binding ability) against PDE of the present invention of the test substance (preferably a compound with a low molecular weight, etc.), and by comparing an inhibitory action (or a binding ability) on other types of PDE, selectivity of the inhibitory action (or the binding ability) can be determined. Accordingly, an inhibitor having a relatively high action toward a specific type of PDE (a selective inhibitor) can be selected. Also, an identification and characterization of an inhibitor become possible.

Hereinafter, the present invention will be explained in more detail by Examples, however, the present invention is not limited to these Examples.

Incidentally, in Examples below, each operation was carried out, unless otherwise specified, according to methods described in "Molecular Cloning" (written by Sambrook, J., Fritsch, E. F. and Maniatis, T., published by Cold Spring Harbor Laboratory Press in 1989), or according to directions attached to commercially available reagents and kits when they were used.

EXAMPLES

Example 1

Isolation of cDNA of Human Novel PDE (PDE11)

(I)

(1) From a comparison of amino acid sequences of catalytic regions of various known PDE molecules, a highly conserved region was chosen, and a sense primer and an anti-sense primer were designed for PCR based on the nucleotide sequence coding this region. As the sense primer, an oligonucleotide was designed comprising a sequence shown by SEQ.ID.NO: 7 of the below mentioned sequence listing, and as the anti-sense primer, an oligonucleotide comprising a sequence shown by SEQ.ID.NO: 8 was designed.

RT-PCR (reverse transcript-polymerase chain reaction) was carried out using these PCR primers to isolate a cDNA fragment from mRNA of human testis.

That is, a reverse transcript reaction was carried out using mRNA of human testis (available from Clontech), RNA PCR kit (GeneAmp RNA PCR Core kit, available from PE Biosystems) and random primer (hexamer) to obtain cDNA. Using the obtained cDNA as a template, PCR reaction was carried out using the above-designed oligonucleotides comprising nucleotide sequences shown in SEQ.ID.NOs: 7 and 8 as a sense primer and an anti-sense primer, respectively. The PCR reaction was repeated for 30 cycles in total, one cycle being carried out under conditions of at 94° C. for 30 sec., at 55° C. for 30 sec., and at 72° C. for 30 sec.

The obtained PCR product was linked to a vector plasmid pGEM-T Easy (available from Promega), and a nucleotide sequence thereof was determined. The nucleotide sequence was determined using an automatic DNA sequencer (ABI PRISM 310, available from PE Biosystems), by dideoxy method (using BigDye terminator cycle sequencing reaction kit available from PE Biosystems) (hereinafter the same as the above). The nucleotide sequence of the thus obtained cDNA fragment was found to be a novel nucleotide sequence which has never been reported, and was found to be a nucleotide sequence with a high homology with a part of a cDNA coding PDE5.

(2) From the cDNA fragment obtained in the above (1), full-length cDNA was obtained by means of RACE method (rapid amplification of cDNA ends) with a procedure described below.

First, based on the information of the nucleotide sequence of cDNA obtained in the above (1), an oligonucleotide comprising a sequence shown in SEQ.ID.NO: 9 of the below mentioned sequence listing was designed as an anti-sense primer, and using this primer and a kit for RACE for elongation of 5' end (5'-RACE) (5'-Full RACE Core Set, available from TaKaRa Shuzo), cDNA fragment was prepared from mRNA of human testis (available from Clontech).

Further, using the prepared cDNA fragment as a template, LA PCR (long and accurate PCR) (using LA PCR Kit, available from TaKaRa Shuzo) was carried out. As the PCR primer, two kinds of oligonucleotides comprising a sequence shown in SEQ.ID.NOs: 10 and 11 of the below mentioned sequence listing for the first amplification, and for the second amplification, two kinds of oligonucleotides comprising a sequences shown in SEQ.ID.Nos: 12 and 13, were used as a sense primer and an anti-sense primer, respectively. Incidentally, each of these 4 kinds of PCR primers were designed according to the information on the nucleotide sequence of cDNA fragment obtained in the above (1).

A nucleotide sequence of the obtained PCR product was determined. Accordingly, it was found that a part of a missing 5' end region was recovered by the above 5'-RACE, and a nucleotide sequence of the recovered 5' end region was confirmed.

Next, by further carrying out 5'-RACE (using Marathon-Ready cDNA (human prostate), available from Clontech) using cDNA derived from human prostate as a template, a 5' region was completely recovered. As a primer, in the first amplification, the first primer (AP1 primer) corresponding to the linker part and a primer comprising a sequence shown in SEQ.ID.NO: 14 of the below mentioned sequence listing, and in the second amplification, the second primer corresponding to the linker part (AP2 primer) and a primer comprising a sequence shown in SEQ.ID.NO: 15 were used, respectively, as a sense primer and an anti-sense primer. These two kinds of anti-sense primers were designed according to the information on the nucleotide sequence of the 5' end region recovered by the above mentioned 5'-RACE.

Next, 3'-RACE was carried out using a kit for RACE for 3' end elongation (3'-RACE) (SMART RACE cDNA Amplification kit, available from Clontech) and mRNA of human thyroid gland (available from Clontech) to completely recover a 3' end region. As a PCR primer for the 3'-RACE, in the first amplification, a primer comprising a sequence shown in SEQ.ID.NO: 16 of the below mentioned sequence and the first primer (UPM primer) corresponding to the linker part, and in the second amplification, a primer comprising a sequence shown in SEQ.ID.NO: 17 and the second primer (NUP primer) corresponding to the linker part were used, respectively, as a sense primer and an anti-sense primer. These two kinds of sense primers were designed according to the information on the nucleotide sequence of cDNA obtained in the above (1).

In any of the above PACEs, PCR reaction was repeated for 5 cycles under conditions at 94° C. for 1 min. followed by at 94° C. for 30 sec. and at 72° C. for 3 min., 5 cycles under conditions at 94° C. for 30 sec., at 70° C. for 30 sec. and at 72° C. for 3 min., and 25 cycles under condition at 94° C. for 30 sec., at 68° C. for 30 sec. and at 72° C. for 3 min.

(3) The nucleotide sequence of the thus obtained full-length cDNA was analyzed and compared with the amino acid sequences of the known PDEs to identify an open reading frame.

Further, based on the information on the nucleotide sequence, PCR primers were designed enclosing an open reading frame, and RT-PCR was carried out as described below, using these primers and mRNA of human prostate.

That is, a reverse transcript reaction was carried out using mRNA of human prostate (available from Clontech), RNA PCR kit (GeneAmp RNA PCR Core kit, available from PE Biosystems) and a random primer (hexamer), to obtain cDNA. Using the thus obtained cDNA as a template, PCR was carried out. As a PCR primer, an oligonucleotide comprising a nucleotide sequence shown in SEQ.ID.Nos: 18 and 19 of the below mentioned sequence listing were used as a sense primer and an anti-sense primer, respectively. PCR reaction was done with one cycle being carried out under conditions of at 94° C. for 30 sec., at 55° C. for 30 sec. and at 72° C. for 5 min.

With respect to plural clones obtained from PCR, nucleotide sequences of cDNA fragments (about 3 kb) were determined, and by comparing each of them, errors made by PCR were corrected to confirm a nucleotide sequence of a full-length cDNA.

(4) The thus obtained full-length cDNA (4476 bp) was thought to be a full-length cDNA of a novel human PDE (referred to as human PDE11 or human PDE11A.) gene. The nucleotide sequence was shown in SEQ.ID.NO: 1 of the below mentioned sequence listing, and an amino acid sequence of a protein encoded thereby, that is, human PDE11 (specifically referred to as human PDE11A1.) was shown in SEQ.ID.NO: 2. A molecular weight of human PDE11 (human PDE11A1) estimated from the amino acid sequence (934 amino acid residues) was about 105 kDa.

Further, from a homology search with the known PDEs with respect to an amino acid sequence, it was assumed that acatalytic domain of the obtained human PDE11 (human PDE11A1) was a region corresponding to the $640^{th}$ to the $881^{st}$ amino acid residues, and that a region comprising a sequence with a high homology to a cGMP binding region reported in a literature (McAllister-Lucus, et al., J. Biol. Chem., Vol 268, pp 22863-22873, 1993) (hereinafter referred to as cGMP binding region) was a region corresponding to the $195^{th}$ to the $403^{rd}$ and the $379^{th}$ to the $591^{st}$ amino acid residues, from a homology of the sequence.

When the amino acid sequence of the human PDE11 (human PDE11A1) was compared to various known human PDEs with cGMP-binding type, homologies in the catalytic domain were 42% with PDE2A, 51% with PDE5A, 44% with PDE6A, 44% with PDE6B, and 43% with PDE10A. Further, homologies in the two cGMP-binding region were, 19 to 47% with PDE2A, PDE5A, PDE6A, PDE6B and PDE1OA, respectively.

Example 2

Isolation of cDNA of Human Novel PDE (PDE11) (II)

(1) cDNA was obtained in the same manner as in the above-stated Example 1 (1).

(2) RACE was carried out to obtain a full-length cDNA from the cDNA fragment obtained in the above (1), according to the procedure described below.

First, in the same manner as in the above Example 1, a part of the 5' end region was recovered.

Next, 5'-RACE was further carried out using cDNA derived from human test is as a template (using Marathon-Ready cDNA (human testis), available from Clontech). As a primer, in the first amplification, the first primer (AP1 primer) corresponding to the linker part and a primer comprising a sequence shown in SEQ.ID.NO: 15 of the below mentioned sequence listing, and in the second amplification, the second primer corresponding to the linker part (AP2primer) and a primer comprising a sequence shown in SEQ.ID.NO: 20 were used, respectively, as a sense primer and an anti-sense primer. These two kinds of anti-sense primers were designed according to the information on the nucleotide sequence of the 5' end region recovered in the above.

Further, 5'-RACE was carried out again in the same manner as in the above, to completely recover the 5' end region. As a primer, in the first amplification, AP1 primer and a primer comprising a sequence shown in SEQ.ID.NO: 21 of the below mentioned sequence listing, and in the second amplification, AP2 primer and a primer comprising a sequence shown in SEQ.ID.NO: 22 were used, respectively, as a sense primer and an anti-sense primer. These two kinds of anti-sense primers were designed according to the information on the nucleotide sequence of the 5' end region recovered by the above mentioned 5'-RACE.

Next, 3'-RACE was carried out in the same manner as in the above Example 1, to completely recover a 3' end region.

(3) After analyzing the nucleotide sequence of the thus obtained full-length cDNA, it was compared to an amino acid sequence of the known PDEs to identify an open reading frame.

Moreover, PCR primers enclosing the open reading frame were designed based on the information on the nucleotide sequence, and RT-PCR was carried out using these primers and mRNA of human testis as follows.

That is, a reverse transcript reaction was carried out using mRNA of human testis (available from Clontech), RNA PCR kit (GeneAmp RNA PCR Core kit, available from PE Biosystems) and random primer (hexamer) to obtain cDNA. Using the obtained cDNA as a template, PCR reaction was carried out. As PCR primers, oligonucleotides comprising nucleotide sequences shown in SEQ.ID.NOs: 23 and 19 were used as a sense primer and an anti-sense primer, respectively. PCR reaction was done with one cycle being carried out under conditions of at 95° C. for 30 sec., at 55° C. for 30 sec. and at 72° C. for 3 min.

With respect to plural clones obtained from PCR, nucleotide sequences of cDNA fragments (about 2.4 kb) were determined, and by comparing each of them, errors made by PCR were corrected to confirm a nucleotide sequence of a full-length cDNA.

(4) The thus obtained full-length cDNA (3507 bp) was thought to be a full-length cDNA of a novel human PDE (referred to as human PDE11 or human PDE11A.) gene. The nucleotide sequence was shown in SEQ.ID.NO: 3 of the below mentioned sequence listing, and an amino acid sequence of a protein encoded thereby, that is, human PDE11 (specifically referred to as human PDE11A2.) was shown in SEQ.ID.NO: 4. A molecular weight of human PDE11 (human PDE11A2) estimated from the amino acid sequence (684 amino acid residues) was about 78 kDa.

The cDNA of human PDE11 (human PDE11A2) obtained in the present Example was assumed to be a splicing variant of the cDNA of human PDE11 (human PDE11Al) obtained in Example 1. Two kinds of PDEs derived from the two kinds of splicing variants, that is, human PDE11Al and human PDE11A2 were different in N terminals of amino acid sequences (the $1^{st}$ to the $304^{th}$ amino acid residues in SEQ.ID.NO: 2 and the $1^{st}$ to the $54^{th}$ amino acid residues in SEQ.ID.NO: 4) and in cDNA sequences corresponding thereto.

Further, from a homology search with known PDEs with respect to an amino acid sequence, it was assumed that a catalytic domain of human PDE11A2 was a region corresponding to the $390^{th}$ to the $631^{st}$ amino acid residues, and that cGMP binding region of human PDE11A2 was a region corresponding to the $129^{th}$ to the $341^{st}$ amino acid residues, from a homology of the sequence. The amino acid sequences in the catalytic domain of human PDE11A2 coincide with those in the catalytic domain of human PDE11A1. Also, the amino acid sequences in the cGMP binding region of human PDE11A2 coincide with those in one of the two cGMP binding regions existing downstream (at 3' side) of the human PDE11A1.

Example 3

Expression and Purification of Human PDE11A1 in COS Cells (1) Construction of a vector plasmid for PDE11A1 Expression With respect to human PDE11A1 obtained in the above Example 1, cDNA fragment amplified in Example 1 (3) was linked to a vector plasmid pGEM-T Easy (available from Promega) to obtain a plasmid pGEM-PDE11PF. Using this pGEM-PDE11PF as a template, PCR was carried out using oligonucleotides comprising a nucleotide sequence shown in SEQ.ID.NOs: 24 and 25 of the below mentioned sequence listing as a sense primer and an anti-sense primer, respectively. Incidentally, these PCR primers were designed based on the $319^{th}$ to $684^{th}$ nucleotide sequence of SEQ.ID.NO: 1 (That is, a nucleotide sequence corresponding to the $1^{st}$ to the $122^{nd}$ amino acid residues of SEQ.ID.NO: 2). cDNA fragment amplified by PCR was linked to pGEM-T Easy (available from Promega) to obtain a plasmid pGEM-PDE11PBM, and its nucleotide sequence was confirmed.

Further, cDNA fragments obtained by treating pGEM-PDE11PF with restriction enzymes KpnI and SalI, and cDNA fragments obtained by treating pGEM-PDE11PBM with restriction enzymes BamHI and KpnI were inserted into a BamHI-XhoI site of an expression vector, pcDNA4/HisMaxC (available from Invitrogen: hereinafter referred to as pHis) to obtain a vector plasmid pHis-PDE11P for PDE11A1 expression.

(2) Transfection of COS Cells

COS-7 cells (ATCC CRL1651) were subcultured in Dulbecco's modified Eagle's medium (available from Life Technologies) to which 10% bovine fetal serum, 100 unit/ml penicillin and 100 μM/streptomycin were added, under conditions of at 37° C. and 5% of carbon dioxide.

COS-7 cells were transfected with the above pHis-PDE11 P (or vector pHis for control). Transfection was carried out using a polycationic liposome agent (LipofectAMINE PLUS: available from Life Technologies).

(3) Purification of Recombinant Human PDE11A1

After 24 hours from transfection, the cells were washed with an ice cold phosphate buffer, and homogenized by ultrasonic treatment in an ice cold homogenizing buffer (40 mM Tris-HCl$_1$, pH 7.5, 1 5 mM benzamidine, 5 μg/ml pepstatin A, 5 μg/ml leupeptin). The obtained homogenate was centrifuged (1000000 g, 60 min.) to collect supernatant.

The above-obtained supernatant was applied to a nickel-nitrotriacetate resin (available from Qiagen) equilibrated with a buffer solution and incubated at 4° C. for 4 hours. This resin was filled in a column (0.8×5 cm) and then, the resin in the column was washed with a washing buffer (40 mM Tris-HCl, pH 7.5, 15 mM benzamidine, 200 mM sodium chloride, 5 mM imidazole, 5 μg/ml pepstatin A, 5 μg/ml leupeptin). Then, proteins were eluted with an eluting buffer (40 mM Tris-HCl, pH7.5, 15 mM benzamidine, 200 mM sodium chloride, 200 mM imidazole, 5 μg/ml pepstatin A, 5 μg/ml leupeptin).

The obtained protein was measured with respect to hydrolysis activity (PDE activity) for cAMP and cGMP, it was found to have a hydrolysis activity for both cAMP and cGMP.

Incidentally, measurement of PDE activity was done according to a radio-labeled nucleotide method. That is, to 500 μl of a buffer for an assay [50 mM Tris-HCl, pH 8.0, 5 mM magnesium chloride, 4 mM 2-mercaptoethanol, 0.33 mg/ml bovine serum albumin (available from Sigma)], containing 1 μM of unlabeled cAMP (or cGMP) and 22 nM of [$^3$H]-cAMP (or [$^3$H]-cGMP) (available from Amersham Pharmacia Biotech), 8~10 μl of the enzyme solution was added to start a reaction. After carrying out a reaction by keeping a temperature at 37° C. for 30 minutes, reaction was terminated by boiling the reaction mixture for 2 minutes, and 100 μl of 1 mg/ml of snake venom (Crotalus atrox snake venom) was further added thereto and the temperature was kept at 37° C. for 30 minutes. Subsequently, 500 μl of methanol was added thereto, and the reaction mixture was applied to Dowex column (1×8-400) Scintillation cocktail was added to each of the eluates, and radioactivity was measured.

Example 4

Expression and Purification of Human PDE11A2 in COS Cells (1) Construction of a Vector Plasmid for PDE11A2 Expression With respect to human PDE11A2 obtained in the above Example 2, cDNA fragment amplified in Example 2 (4) was linked to a vector plasmid pGEM-TEasy (available from Promega) to obtain a plasmid pGEM-PDE11TF. Using this pGEM-PDE11TF as a template, PCR was carried out using oligonucleotides comprising a nucleotide sequence shown in SEQ.ID.NOs: 26 and 27 of the below mentioned sequence listing as a sense primer and an anti-sense primer, respectively. Incidentally, these PCR primers were designed based on the $100^{th}$ to $417^{th}$ nucleotide sequence of SEQ.ID.NO: 3 (That is, a nucleotide sequence corresponding to the $1^{st}$ to the $106^{th}$ amino acid residues of SEQ.ID.NO: 4). cDNA fragment amplified by PCR was linked to pGEM-T Easy (available from Promega) to obtain a plasmid pGEM-PDE11TBM, and its nucleotide sequence was confirmed.

Further, cDNA fragments obtained by treating pGEM-PDE11TF with restriction enzymes SacI and EcoRV, and EcoRV and SalI, cDNA fragments obtained by treating pGEM-PDE11TBM with restriction enzymes BamHI and SacI were inserted into a BamHI-XhoI site of an expression vector, pHis, to obtain a vector plasmid pHis-PDE11T for PDE11A2 expression.

(2) Transfection of COS Cells

COS-7 cells which were subcultured under the same conditions as in the above Example 3 (2) were transfected with the above-mentioned pHis-PDE11T (or vector pHis for control) in the same manner as in the above Example 3 (2).

(3) Purification of Recombinant Human PDE11A2

Purification of recombinant human PDE11A2 was carried out in the same manner as in the above Example 3 (3). Also, when its PDE activity was measured in the same manner as in the above Example 3 (3), it was found to have a hydrolysis activity for both cAMP and cGMP.

Example 5

Analysis of Enzymatic Properties of Human PDE11

Using each of the purified recombinant human PDE11A1 obtained in Example 3 and the purified recombinant human PDE11A2 obtained in Example 4, various enzymatic properties of human PDE11 were analyzed.

(1) Kinetic Analysis of Enzyme Reaction

Enzyme reactions were carried out using a substrate (cAMP or cGMP) of various concentrations, to measure PDE activity (initial reaction rate). Enzyme reaction and PDE activity measurement were done in the same manner as in the above Example 3 (3), provided that, in a reaction mixture, a concentration of unlabeled cAMP (or cGMP) was set to be 0.1 to 10 µM.

Figure 2:
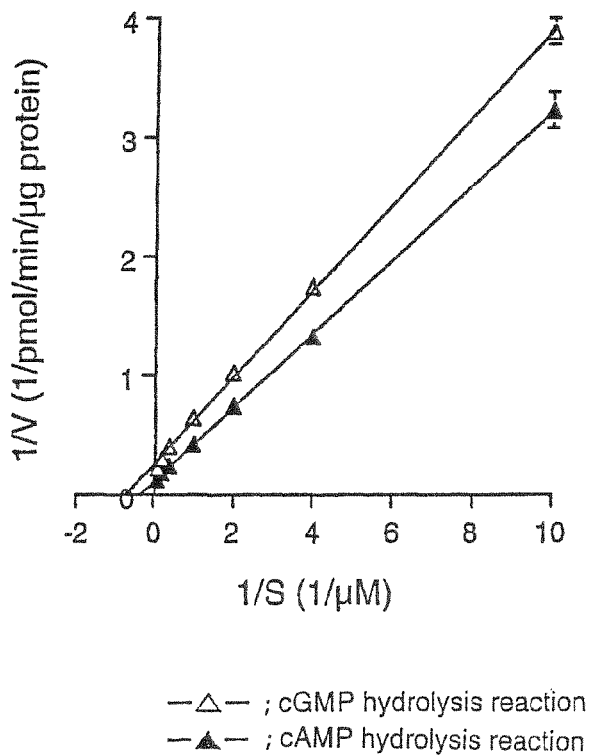
FIG. 2 shows a result of a kinetic analysis on hydrolysis of cAMP or cGMP by human PDE11A2 (Lineweaver-Burk plot).

The results (Lineweaver-Burk plot) are shown in FIG. 1 for human PDE11A1 and FIG. 2 for human PDE11A2.

From the analysis, Km value of human PDE11A1 was 2.96±0.4 5 7 µM, and Vmax was 267±47.9 pmol/min/µg of protein, when cAMP was a substrate. On the other hand, Km value of human PDE11A1 was 1.43±0.109 µM and Vmax was 121±8.08 pmol/min/µg protein, when cGMP was a substrate.

Km value of human PDE11A2 was 2.99±0.488 µM and Vmax was 9.63±1.88 pmol/min/µg protein, when cAMP was a substrate. On the other hand, Km value of human PDE11A2 was 1.47±0.115 µM and Vmax was 4.02±0.214 p mol/min/µg of protein, when cGMP was a substrate.

From the above, it was found that although human PDE11 has an activity of hydrolyzing both cAMP and cGMP, it has a higher affinity for cGMP.

(2) Influence of cGMP on cAMP Hydrolysis Activity and Influence of cAMP on cGMP Hydrolysis Activity It was studied how an addition of cGMP of various concentrations to a reaction mixture would affect cAMP hydrolysis activity. It was also studied how an addition of cAMP of various concentrations to a reaction mixture would affect cGMP hydrolysis activity.

Figure 3:
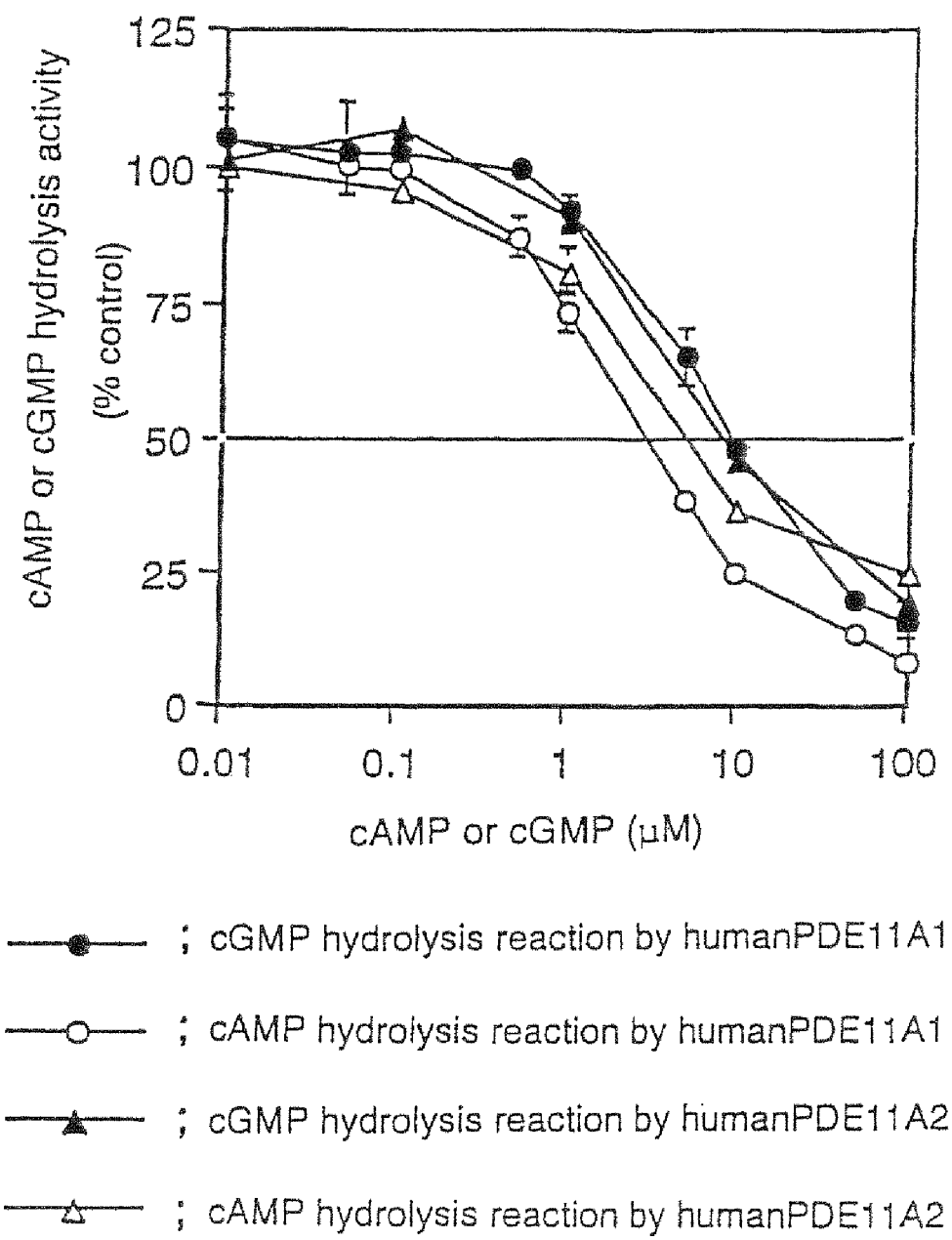
FIG. 3 shows a result of studies on an influence of cGMP on cAMP hydrolysis activity, and an influence of cAMP on cGMP hydrolysis activity, with respect to the human PDE11A1 and the human PDE11A2, wherein relative values (%) of activity are shown, taking a cAMP hydrolysis activity without adding CGMP, or a cGMP hydrolysis activity without adding cAMP as 100%.

Enzyme reaction and PDE activity measurement were done in the same manner as in the above Example 3 (3), except that in an experiment for measuring cAMP hydrolysis activity, 3.5 µM of unlabeled cAMP was added, and 0.01~100 µM of cGMP (unlabeled) was added (or was not added). On the other hand, in an experiment for measuring cGMP hydrolysis activity, 1.3 µM of unlabeld cGMP was added, and 0.01~100 µM of cAMP (unlabeled) was added (or was not added).

cAMP hydrolysis activity was calculated as a relative value (%) taking an activity measured without adding cGMP as 100%. Also, cGMP hydrolysis activity was calculated as a relative value (%) taking an activity measured without adding cAMP as 100%. The results are shown in FIG. 3. It is clearly confirmed in FIG. 3 that, in case of human PDE11, cAMP hydrolysis activity was lowered depending on a concentration of CGMP added, while cGMP hydrolysis activity was lowered depending on a concentration of cAMP added.

(3) Inhibition of Activity by Various known PDE Inhibitors

Effects of various known PDE inhibitors [IBMX, Vinpocetine, EHNA. Milrinone, Rolipram, Zaprinast, Dipyridamole, SCH51866, and E4021] on a cAMP and cGMP hydrolysis activity (PDE activity) of human PDE11 were studied as follows.

Enzyme reaction was carried out using cAMP or cGMP as a substrate, and various kinds of known PDE inhibitors were added in the reaction mixture to measure a hydrolysis activity. Enzyme reaction and measurement of PDE activity was done in the same manner as in the above Example 3 (3), except that, in the reaction mixture, in case of adding unlabeled cAMP, a concentration was 3.5 µM, and in case of adding unlabeled cGMP, a concentration was 1.3 µM, and various kinds of known PDE inhibitors were added in an amount of 0~100 µM.

Inhibitory actions of various PDE inhibitors on an activity of human PDE11 expressed in terms of IC 50 are shown in Table 1 for human PDE11A1 and Table 2 for human PDE11A2, respectively.

TABLE 1

| | IC50 value (µM) for human PDE11A1 activity | |
|---|---|---|
| Inhibitor | Effect on cAMP hydrolysis activity | Effect on cGMP hydrolysis activity |
| IBMX | 65 ± 13 | 81 ± 16 |
| Vinpocetine | >100 | >100 |
| EHNA | >100 | >100 |
| Milrinone | >100 | >100 |
| Rolipram | >100 | >100 |
| Zaprinast | 26 ± 6.8 | 33 ± 5.3 |
| Dipyridamole | 0.82 ± 0.28 | 0.72 ± 0.08 |
| SCH51866 | 22 ± 1.8 | 25 ± 5.8 |
| E4021 | 1.8 ± 0.33 | 1.8 ± 0.25 |

TABLE 2

| | IC50 value (µM) for human PDE11A2 activity | |
|---|---|---|
| Inhibitor | Effect on cAMP hydrolysis activity | Effect on cGMP hydrolysis activity |
| IBMX | 30 ± 3.9 | 38 ± 3.5 |
| Vinpocetine | 49 ± 9.2 | 68 ± 4.0 |

TABLE 2-continued

| | IC50 value (μM) for human PDE11A2 activity | |
|---|---|---|
| Inhibitor | Effect on cAMP hydrolysis activity | Effect on cGMP hydrolysis activity |
| EHNA | >100 | >100 |
| Milrinone | >100 | >100 |
| Rolipram | >100 | >100 |
| Zaprinast | 18 ± 1 0 | 11 ± 3.6 |
| Dipyridamole | 0.36 ± 0.11 | 0.34 ± 0.09 |
| SCH51866 | 11 ± 4.8 | 8.6 ± 2.7 |
| E4021 | 0.88 ± 0.13 | 0.66 ± 0.19 |

Example 6

Expressions of PDE11 in Various Tissues of Human

Various kinds of human tissues were examined whether or not PDE11 gene was expressed as follows.

Using mRNAs of various human tissues (Human Multiple Tissue Expression Array: available from Clontech) dot blot analysis was done with respect to mRNAs of tissues and organs as shown in FIG. 4. As a probe, a DNA fragment obtained in the above Examples 1 and 2 coding a part of human PDE11A (a nucleotide sequence of the fragment corresponds to the $1237^{th}$ to the $1801^{st}$ nucleotide sequence of the human PDE11A1 cDNA shown in SEQ.ID.NO: 1, and also corresponds to the $268^{th}$ to the $832^{nd}$ nucleotide sequence of the human PDE11A2 cDNA shown in SEQ.ID.NO: 3.) was used by labeling with 32P. In addition, an amount of mRNA was controlled to make signal for probes constant, when cDNA of human ubiquitin and major histocompatibility complex class Ic were taken as probes.

Hybridization was carried out under conditions described below. That is, a nylon membrane was placed in a hybridization solution containing a probe labeled with $^{32}$P (50% formamide, 4×SSC, 0.5% SDS, 5×Denhardt's solution, 100 μg/ml salmon sperm DNA) at 42° C. for 20 hours for hybridization to proceed. Subsequently, the membrane was washed with washing solution A (0.5×SSC, 0.1% SDS) at room temperature for 3 min. and further washed with washing solution B (0.2×SSC, 0.1% SDS) at 60° C. for 30 min. for twice. Subsequently, autoradiography was carried out at −80° C. for 3 days.

The result of dot blotting, as shown in FIG. 4, strong expressions of PDE11 mRNA were detected in prostate and testis. Also, slightly weak expressions were detected in salivary gland, pituitary gland, thyroid gland and liver (order of intensity of expression was in order of the description).

Further, with respect to mRNA of human testis and human prostate, Northern blot analysis was done using the same probe as the above and under the same conditions.

As a result of Northern blotting analysis, a band of about 3 kb was detected in testis, and in prostate, bands of about 2 kb, about 6 kb and about 10 kb were observed.

Example 7

Isolation of cDNA of Novel Rat PDE (PDE11) (I)

(1) Based on the information on the nucleotide sequence of the cDNA of human PDE11A obtained in the above Examples 1 and 2, PCR primers were designed, and RT-PCR was carried out using these to isolate cDNA of PDE11 from mRNA of rat testis.

That is, reverse transcript reaction was carried out using mRNA of rat testis (available from Wako Junyaku), RNA PCR kit (available from PE Biosystems, GeneAmp RNA PCR Core kit) and random primer (hexamer) to obtain cDNA. Using the obtained cDNA as a template, PCR was carried out. As PCR primers, oligonucleotides comprising nucleotide sequences shown in SEQ.ID.NOs: 28 and 29 of the below mentioned sequence listing were used as a sense primer and an anti-sense primer, respectively. The PCR reaction was repeated for 30 cycles in total, one cycle being carried out under conditions of at 95° C. for 30 sec., at 54° C. for 30 sec., and at 72° C. for 2 min.

A nucleotide sequence of the cDNA fragment amplified by PCR was determined.

(2) In order to obtain full-length cDNA from the cDNA fragment obtained in the above (1), 5'-RACE and 3'-RACE were done using mRNA of rat testis (available from Wako Junyaku) according to the below described procedures. For RACE, a kit for RACE (available from Clontech, SMART RACE cDNA Amplification kit) was used.

First, 5'-RACE was done to recover a part of 5' end region. As primers, in the first amplification, the first primer (UPM primer) corresponding to the linker part and a primer comprising a sequence shown in SEQ.ID.NO: 30 of the below mentioned sequence listing, and in the second amplification, the second primer corresponding to the linker part (NUP primer) and a primer comprising a sequence shown in SEQ.ID.NO: 31 were used, respectively, as a sense primer and an anti-sense primer. These two kinds of anti-sense primers were designed according to the information on the nucleotide sequence of the cDNA obtained in the above (1).

5'-RACE was further carried out to completely recover the 5' end region. As primers, in the first amplification, the UPM primer and a primer comprising a sequence shown in SEQ.ID.NO: 32 of the below mentioned sequence listing, and in the second amplification, the NUP primer and a primer comprising a sequence shown in SEQ.ID.NO: 33 were used, respectively, as a sense primer and an anti-sense primer. These two kinds of anti-sense primers were designed according to the information on the nucleotide sequence of the above-recovered 5' end region.

Next, 3-RACE was done to completely recovera 3' end region. As primers, in the first amplification, a primer comprising a sequence shown in SEQ.ID.NO: 34 of the below mentioned sequence listing and the UPM primer, and in the second amplification, a primer comprising a sequence shown in SEQ.ID.NO: 35 and the NUP primer were used, respectively, as a sense primer and an anti-sense primer. These two kinds of anti-sense primers were designed according to the information on the nucleotide sequence of the cDNA fragment obtained in the above (1).

(3) After analyzing the nucleotide sequence of the thus obtained full-length cDNA, it was compared to an amino acid sequence of the known PDE to identify an open reading frame.

Further, PCR primers enclosing the open reading frame were designed based on the information on the nucleotide sequence, and RT-PCR was carried out using these primers and mRNA of rat testis as follows.

That is, a reverse transcription reaction was carried out using mRNA of rat testis (available from Wako Junyaku), RNA PCR kit (GeneAmp RNA PCR Core kit, available from PE Biosystems) and a polydT-tailed primer to obtain cDNA. Using the obtained cDNA as a template, PCR reaction was carried out. As a PCR primer, oligonucleotides comprising nucleotide sequences shown in SEQ.ID.NOs: 36 and 37 were used as a sense primer and an anti-sense primer, respectively.

PCR reaction was repeated for 30 cycles in total, one cycle being carried out under conditions of at 95° C. for 30 sec., at 57° C. for 30 sec. and at 72° C. for 3 min.

With respect to plural clones obtained from PCR, nucleotide sequences of cDNA fragments (about 2.3 kb) were determined, and by comparing each of them, errors made by PCR were corrected to confirm a nucleotide sequence of a full-length cDNA.

(4) The thus obtained full-length cDNA (3492 bp) was thought to be a full-length cDNA of a novel rat PDE (referred to as rat PDE11 or rat PDE11A.) gene. The nucleotide sequence was shown in SEQ.ID.NO: 5 of the below mentioned sequence listing, and an amino acid sequence of a protein encoded thereby, that is, rat PDE11 (specifically referred to as rat PDE11A2.) was shown in SEQ.ID.NO: 6. A molecular weight of rat PDE11 (rat PDE11A2) estimated from the amino acid sequence (685 amino acid residues) was about 78 kDa.

When the amino acid sequence of rat PDE11 (rat PDE11A2) was compared to the amino acid sequence of human PDE11A2 obtained in Example 2, a homology as high as about 93% was confirmed.

Example 8

Isolation of cDNA of Novel Rat PDE (PDE11) (II)

(1) 5'-RACE was carried out using cDNA derived from rat liver (available from Clontech, Marathon-Ready cDNA (rat liver) was used). As primers, in the first amplification, the first primer (AP1 primer) corresponding to the linker part and a primer comprising a sequence shown in SEQ.ID.NO: 32 of the below mentioned sequence listing, and in the second amplification, the second primer corresponding to the linker part (AP2 primer) and a primer comprising a sequence shown in SEQ.ID.NO: 33 were used, respectively, as a sense primer and an anti-sense primer. These two kinds of anti-sense primers were designed according to the information on the nucleotide sequence of the cDNA of the rat PDE11 (rat PDE11A2) obtained in the above Example 7.

5'-RACE was further carried out using the cDNA of rat liver (available from Clontech, Marathon-Ready cDNA (rat liver) was used) to completely recover the 5' end region. As primers, in the first amplification, the AP1 primer and a primer comprising a sequence shown in SEQ.ID.NO: 40 of the below mentioned sequence listing, and in the second amplification, the AP2 primer and a primer comprising a sequence shown in SEQ.ID.NO: 41 were used, respectively, as a sense primer and an anti-sense primer. These two kinds of anti-sense primers were designed according to the information on the nucleotide sequence of the 5' end region recovered in the above 5'-RACE.

(2) After analyzing the nucleotide sequence of the thus obtained full-length cDNA, it was compared to an amino acid sequence of the known PDE to identify an open reading frame.

Further, PCR primers enclosing the open reading frame were designed based on the information on the nucleotide sequence, and RT-PCR was carried out using these primers and mRNA derived from rat liver as follows.

That is, a reverse transcript reaction was carried out using mRNA of rat liver (available from Clontech), RNA PCR kit (GeneAmp RNA PCR Core kit, available from PE Biosystems) and random primer (hexamer) to obtain cDNA. Using the obtained cDNA as a template, PCR reaction was carried out. As PCR primers, oligonucleotides comprising nucleotide sequences shown in SEQ.ID.NOs: 42 and 37 were used as a sense primer and an anti-sense primer, respectively. PCR reaction was repeated for 30 cycles in total, one cycle being carried out under conditions of at 95° C. for 30 sec., at 57° C. for 30 sec. and at 72° C. for 4 min.

With respect to plural clones obtained from PCR, nucleotide sequences of cDNA fragments (about 3.0 kb) were determined, and by comparing each of them, errors made by PCR were corrected to determine a nucleotide sequence of a full-length cDNA.

(3) The thus obtained full-length cDNA (4170 bp) was thought to be a full-length cDNA of a novel rat PDE (rat PDE11A) gene. The nucleotide sequence was shown in SEQ.ID.NO: 38 of the below mentioned sequence listing, and an amino acid sequence of a protein encoded thereby, that is, rat PDE11 (specifically referred to as rat PDE11A1.) was shown in SEQ.ID.NO: 39. A molecular weight of rat PDE11 (rat PDE11A1) estimated from the amino acid sequence (935 amino acid residues) was about 105 kDa.

When the amino acid sequence of rat PDE11 (rat PDE11A1) was compared to the amino acid sequence of human PDE11A1 obtained in Example 1, a homology of as high as about 94% was confirmed.

INDUSTRIAL APPLICABILITY

The novel PDE of the present invention and the gene thereof are useful for study of a complex mechanism of intracellular signal transduction. Also, it can possibly serve as a target compound of a therapeutic agent for novel disease.

Additionally, a method for characterizing, identifying and selecting an inhibitor, using the novel PDE of the present invention and the gene thereof is useful for development of an inhibitor with a high selectivity and an excellent pharmaceutical with a high therapeutic effect and less side effect.

What is claimed is:

1. An isolated nucleic acid which encodes a protein having an activity of hydrolyzing a cyclic nucleotide, wherein said protein is
a protein having the amino acid sequence of SEQ ID NO:2.

2. The isolated nucleic acid according to claim 1, wherein said nucleic acid has the nucleotide sequence of SEQ ID NO: 1.

3. The isolated nucleic acid according to claim 1, wherein said nucleic acid comprises nucleotides 319 to 1230 of SEQ ID NO:1.

4. The isolated nucleic acid according to claim 1, wherein said nucleic acid includes regions coding for two cGMP-binding regions comprising nucleotides 901 to 1527 of SEQ ID NO:1 and nucleotides 1453 to 2091 of SEQ ID NO:1.

5. The isolated nucleic acid according to claim 1, 2, 3 or 4, wherein said nucleic acid is a human nucleic acid.

6. A recombinant vector comprising the nucleic acid of claim 1, 2, 3 or 4.

7. A recombinant vector according to claim 6, wherein said vector is an expression vector.

8. A host cell comprising the recombinant vector of claim 6.

9. A method for detecting expression of a phosphodiesterase gene, which comprises using the nucleic acid of claim 2 as a probe, and detecting the expression of the phosphodiesterase gene.

* * * * *

SEQUENCE LISTING

```
<160> NUMBER OF SEQ ID NOS: 42

<210> SEQ ID NO 1
<211> LENGTH: 4476
<212> TYPE: DNA
<213> ORGANISM: Homo sapiens
<220> FEATURE:
<221> NAME/KEY: CDS
<222> LOCATION: (319)..(3120)

<400> SEQUENCE: 1
gcagcggcgg  cagccagaac  aggagcagcg  atagctcggg  tttccggaac  aggagccggg      60
```

```
gcagcggcgg cagctcagtg ctgggcacct gtgcggagca ggagtagcag gaccacgggg      120
tggggtcggc gccagccact ctgagccaga aaggaaggg gcatctccca gattccactg        180 ctggaataa tctccagggg aggtggcgct gaactgggaa tactggtggg ggtgaacatg       240
tgcaggaaca gctagaggcc tcggggcagg aaaacatttg gttcacgtgt aaacaggcaa     300
ggaaagctgt ctgggacc atg gca gcc tcc cgc ctg gac ttt ggg gag gtg         351
                    Met Ala Ala Ser Arg Leu Asp Phe Gly Glu Val
                     1               5                       10 gaa act ttc ctg gac agg cac cca gag ttg ttt gaa gat tac ttg atg         399
Glu Thr Phe Leu Asp Arg His Pro Glu Leu Phe Glu Asp Tyr Leu Met
         15                  20                  25 cgg aag ggg aag cag gag atg gtt gaa aag tgg ctg cag agg cac agt         447
Arg Lys Gly Lys Gln Glu Met Val Glu Lys Trp Leu Gln Arg His Ser
     30                  35                  40 cag ggt cag ggg gct tta ggt cca agg ccc tct ttg gct ggt acc agc         495
Gln Gly Gln Gly Ala Leu Gly Pro Arg Pro Ser Leu Ala Gly Thr Ser
 45                  50                  55 agc ttg gct cac agc acc tgc aga ggt ggc agc agc gtt ggt ggt ggc         543
Ser Leu Ala His Ser Thr Cys Arg Gly Gly Ser Ser Val Gly Gly Gly
 60                  65                  70                  75 act gga cca aat ggc tct gcc cac agc cag ccc ctt ccc ggt ggc ggg         591
Thr Gly Pro Asn Gly Ser Ala His Ser Gln Pro Leu Pro Gly Gly Gly
                 80                  85                  90 gac tgt ggt ggg gtt ccc ttg agt ccc agc tgg gcc ggt ggc agc agg         639
Asp Cys Gly Gly Val Pro Leu Ser Pro Ser Trp Ala Gly Gly Ser Arg
                 95                 100                 105 ggc gat ggg aac ctg cag cgg aga gct tct cag aaa gag cta agg aag         687
Gly Asp Gly Asn Leu Gln Arg Arg Ala Ser Gln Lys Glu Leu Arg Lys
        110                 115                 120 agt ttt gcc cgc tcc aag gcc atc cac gtg aac agg acc tac gat gaa         735
Ser Phe Ala Arg Ser Lys Ala Ile His Val Asn Arg Thr Tyr Asp Glu
    125                 130                 135 cag gtg acc tcc cgg gct cag gaa ccc ctg agt agt gta cga cgg agg         783
Gln Val Thr Ser Arg Ala Gln Glu Pro Leu Ser Ser Val Arg Arg Arg
140                 145                 150                 155 gca ctt ctc cgg aag gca agc tcc ctg ccc ccc acc aca gcc cat att         831
Ala Leu Leu Arg Lys Ala Ser Ser Leu Pro Pro Thr Thr Ala His Ile
                160                 165                 170 ctc agt gcg ctg ctg gaa tcg aga gtg aat ctg cct cag tat ccc cct         879
Leu Ser Ala Leu Leu Glu Ser Arg Val Asn Leu Pro Gln Tyr Pro Pro
            175                 180                 185 aca gcc atc gac tac aag tgc cat ctg aaa aag cat aat gag cgt cag         927
Thr Ala Ile Asp Tyr Lys Cys His Leu Lys Lys His Asn Glu Arg Gln
            190                 195                 200 ttc ttt ctg gaa ttg gtc aaa gat atc tcc aat gac ctt gac ctc acc         975
Phe Phe Leu Glu Leu Val Lys Asp Ile Ser Asn Asp Leu Asp Leu Thr
    205                 210                 215 agc ctg agc tac aag att ctc atc ttt gtc tgc ctt atg gtg gat gct        1023
Ser Leu Ser Tyr Lys Ile Leu Ile Phe Val Cys Leu Met Val Asp Ala
220                 225                 230                 235 gac cgc tgc tct ctt ttc ctg gtg gaa ggg gca gct gct ggc aag aag        1071
Asp Arg Cys Ser Leu Phe Leu Val Glu Gly Ala Ala Ala Gly Lys Lys
                240                 245                 250 acc ttg gtc tcc aaa ttc ttt gat gtg cat gca gga acc cct ctg ctg        1119
Thr Leu Val Ser Lys Phe Phe Asp Val His Ala Gly Thr Pro Leu Leu
                255                 260                 265 cct tgc agc agc aca gag aac tca aat gag gtg cag gtc ccc tgg ggc        1167
Pro Cys Ser Ser Thr Glu Asn Ser Asn Glu Val Gln Val Pro Trp Gly
            270                 275                 280
```

|  |  |
|---|---:|
| aaa ggt atc att ggc tat gtc ggg gag cat gga gaa acg gtc aac att<br>Lys Gly Ile Ile Gly Tyr Val Gly Glu His Gly Glu Thr Val Asn Ile<br>285                     290                     295 | 1215 |
| cct gat gcc tac cag gat cga cga ttc aat gat gaa atc gac aag cta<br>Pro Asp Ala Tyr Gln Asp Arg Arg Phe Asn Asp Glu Ile Asp Lys Leu<br>300                   305                   310                   315 | 1263 |
| act gga tac aag aca aaa tca tta ttg tgc atg cct atc cga agc agt<br>Thr Gly Tyr Lys Thr Lys Ser Leu Leu Cys Met Pro Ile Arg Ser Ser<br>                   320                   325                   330 | 1311 |
| gat ggt gag att att ggt gtg gcc caa gcg ata aat aag att cct gaa<br>Asp Gly Glu Ile Ile Gly Val Ala Gln Ala Ile Asn Lys Ile Pro Glu<br>                335                  340                   345 | 1359 |
| gga gct cca ttt act gaa gat gat gaa aaa gtt atg cag atg tat ctt<br>Gly Ala Pro Phe Thr Glu Asp Asp Glu Lys Val Met Gln Met Tyr Leu<br>350                     355                   360 | 1407 |
| cca ttt tgt gga atc gcc ata tct aac gct cag ctc ttt gct gcc tca<br>Pro Phe Cys Gly Ile Ala Ile Ser Asn Ala Gln Leu Phe Ala Ala Ser<br>365                     370                   375 | 1455 |
| agg aaa gaa tat gaa aga agc aga gct ttg cta gag gtg gtt aat gac<br>Arg Lys Glu Tyr Glu Arg Ser Arg Ala Leu Leu Glu Val Val Asn Asp<br>380                     385                   390                   395 | 1503 |
| ctc ttt gaa gaa cag act gac ctg gag aaa att gtc aag aaa ata atg<br>Leu Phe Glu Glu Gln Thr Asp Leu Glu Lys Ile Val Lys Lys Ile Met<br>                   400                   405                   410 | 1551 |
| cat cgg gcc caa act ctg ctg aaa tgt gaa cgc tgt tct gtt tta ctc<br>His Arg Ala Gln Thr Leu Leu Lys Cys Glu Arg Cys Ser Val Leu Leu<br>                415                  420                   425 | 1599 |
| cta gag gac atc gaa tca cca gtg gtg aaa ttt acc aaa tcc ttt gaa<br>Leu Glu Asp Ile Glu Ser Pro Val Val Lys Phe Thr Lys Ser Phe Glu<br>430                     435                   440 | 1647 |
| ttg atg tcc cca aag tgc agt gct gat gct gag aac agt ttc aaa gaa<br>Leu Met Ser Pro Lys Cys Ser Ala Asp Ala Glu Asn Ser Phe Lys Glu<br>445                     450                   455 | 1695 |
| agc atg gag aaa tca tca tac tcc gac tgg cta ata aat aac agc att<br>Ser Met Glu Lys Ser Ser Tyr Ser Asp Trp Leu Ile Asn Asn Ser Ile<br>460                     465                   470                   475 | 1743 |
| gct gag ctg gtt gct tca aca ggc ctt cca gtg aac atc agt gat gcc<br>Ala Glu Leu Val Ala Ser Thr Gly Leu Pro Val Asn Ile Ser Asp Ala<br>                   480                   485                   490 | 1791 |
| tac cag gat ccg cgc ttt gat gca gag gca gac cag ata tct ggt ttt<br>Tyr Gln Asp Pro Arg Phe Asp Ala Glu Ala Asp Gln Ile Ser Gly Phe<br>                495                  500                   505 | 1839 |
| cac ata aga tct gtt ctt tgt gtc cct att tgg aat agc aac cac caa<br>His Ile Arg Ser Val Leu Cys Val Pro Ile Trp Asn Ser Asn His Gln<br>510                     515                   520 | 1887 |
| ata att gga gtg gct caa gtg tta aac aga ctt gat ggg aaa cct ttt<br>Ile Ile Gly Val Ala Gln Val Leu Asn Arg Leu Asp Gly Lys Pro Phe<br>525                     530                   535 | 1935 |
| gat gat gca gat caa cga ctt ttt gag gct ttt gtc atc ttt tgt gga<br>Asp Asp Ala Asp Gln Arg Leu Phe Glu Ala Phe Val Ile Phe Cys Gly<br>540                     545                   550                   555 | 1983 |
| ctt ggc atc aac aac aca att atg tat gat caa gtg aag aag tcc tgg<br>Leu Gly Ile Asn Asn Thr Ile Met Tyr Asp Gln Val Lys Lys Ser Trp<br>                   560                   565                   570 | 2031 |
| gcc aag cag tct gtg gct ctt gat gtg cta tca tac cat gca aca tgt<br>Ala Lys Gln Ser Val Ala Leu Asp Val Leu Ser Tyr His Ala Thr Cys<br>                575                  580                   585 | 2079 |
| tca aaa gct gaa gtt gac aag ttt aag gca gcc aac atc cct ctg gtg<br>Ser Lys Ala Glu Val Asp Lys Phe Lys Ala Ala Asn Ile Pro Leu Val<br>590                     595                   600 | 2127 |

```
tca gaa ctt gcc atc gat gac att cat ttt gat gac ttt tct ctc gac    2175
Ser Glu Leu Ala Ile Asp Asp Ile His Phe Asp Asp Phe Ser Leu Asp
    605                 610                 615 gtt gat gcc atg atc aca gct gct ctc cgg atg ttc atg gag ctg ggg    2223
Val Asp Ala Met Ile Thr Ala Ala Leu Arg Met Phe Met Glu Leu Gly
620                 625                 630                 635 atg gta cag aaa ttt aaa att gac tat gag aca ctg tgt agg tgg ctt    2271
Met Val Gln Lys Phe Lys Ile Asp Tyr Glu Thr Leu Cys Arg Trp Leu
                640                 645                 650 ttg aca gtg agg aaa aac tat cgg atg gtt cta tac cac aac tgg aga    2319
Leu Thr Val Arg Lys Asn Tyr Arg Met Val Leu Tyr His Asn Trp Arg
            655                 660                 665 cat gcc ttc aac gtg tgt cag ctg atg ttc gcg atg tta acc act gct    2367
His Ala Phe Asn Val Cys Gln Leu Met Phe Ala Met Leu Thr Thr Ala
        670                 675                 680 ggg ttt caa gac att ctg acc gag gtg gaa att tta gcg gtg att gtg    2415
Gly Phe Gln Asp Ile Leu Thr Glu Val Glu Ile Leu Ala Val Ile Val
685                 690                 695 gga tgc ctg tgt cat gac ctc gac cac agg gga acc aac aat gcc ttc    2463
Gly Cys Leu Cys His Asp Leu Asp His Arg Gly Thr Asn Asn Ala Phe
700                 705                 710                 715 caa gct aag agt ggc tct gcc ctg gcc caa ctc tat gga acc tct gct    2511
Gln Ala Lys Ser Gly Ser Ala Leu Ala Gln Leu Tyr Gly Thr Ser Ala
                720                 725                 730 acc ttg gag cat cac cat ttc aac cac gcc gtg atg atc ctt caa agt    2559
Thr Leu Glu His His His Phe Asn His Ala Val Met Ile Leu Gln Ser
            735                 740                 745 gag ggt cac aat atc ttt gct aac ctg tcc tcc aag gaa tat agt gac    2607
Glu Gly His Asn Ile Phe Ala Asn Leu Ser Ser Lys Glu Tyr Ser Asp
        750                 755                 760 ctt atg cag ctt ttg aag cag tca ata ttg gca aca gac ctc acg ctg    2655
Leu Met Gln Leu Leu Lys Gln Ser Ile Leu Ala Thr Asp Leu Thr Leu
765                 770                 775 tac ttt gag agg aga act gaa ttc ttt gaa ctt gtc agt aaa gga gaa    2703
Tyr Phe Glu Arg Arg Thr Glu Phe Phe Glu Leu Val Ser Lys Gly Glu
780                 785                 790                 795 tac gat tgg aac atc aaa aac cat cgt gat ata ttt cga tca atg tta    2751
Tyr Asp Trp Asn Ile Lys Asn His Arg Asp Ile Phe Arg Ser Met Leu
                800                 805                 810 atg aca gcc tgt gac ctt gga gcc gtg acc aaa ccg tgg gag atc tcc    2799
Met Thr Ala Cys Asp Leu Gly Ala Val Thr Lys Pro Trp Glu Ile Ser
            815                 820                 825 aga cag gtg gca gaa ctt gta acc agt gag ttc ttc gaa caa gga gat    2847
Arg Gln Val Ala Glu Leu Val Thr Ser Glu Phe Phe Glu Gln Gly Asp
        830                 835                 840 cgg gag aga tta gag ctc aaa ctc act cct tca gca att ttt gat cgg    2895
Arg Glu Arg Leu Glu Leu Lys Leu Thr Pro Ser Ala Ile Phe Asp Arg
845                 850                 855 aac cgg aag gat gaa ctg cct cgg ttg caa ctg gag tgg att gat agc    2943
Asn Arg Lys Asp Glu Leu Pro Arg Leu Gln Leu Glu Trp Ile Asp Ser
860                 865                 870                 875 atc tgc atg cct ttg tat cag gca ctg gtg aag gtc aac gtg aaa ctg    2991
Ile Cys Met Pro Leu Tyr Gln Ala Leu Val Lys Val Asn Val Lys Leu
                880                 885                 890 aag ccg atg cta gat tca gta gct aca aac aga agt aag tgg gaa gag    3039
Lys Pro Met Leu Asp Ser Val Ala Thr Asn Arg Ser Lys Trp Glu Glu
            895                 900                 905 cta cac caa aaa cga ctg ctg gcc tca act gcc tca tcc tcc tcc cct    3087
Leu His Gln Lys Arg Leu Leu Ala Ser Thr Ala Ser Ser Ser Ser Pro
        910                 915                 920
```

```
gcc agt gtt atg gta gcc aag gaa gac agg aac taaacctcca ggtcagctgc    3140
Ala Ser Val Met Val Ala Lys Glu Asp Arg Asn
    925                 930 agctgcaaaa tgactacagc ctgaagggcc attttcagtc cagcaatgtc atccttttgt    3200
tcttttagct cagaaagacc taacatctca aggatgcact gggaaccatg cctgggcttt    3260
caccttgaag catggtcagc agcagagaga gcaacgggaa ggacaaagaa agaggtgggg    3320
cagggagcac accccaggac cctcactttt ccctaatgaa cacgcatggg ctgaaatgaa    3380
ggctctgggt aggggactgt tttggatcca aggacctgtg gacagtcggc ctacttactc    3440
tgagctgagg gaacactgaa cagtaaaagc gtcattagcg ctgcttcatt ttgtataggg    3500
cttttctgtt tgttacaagc caaacattgc ctgtctttgc ttcccgtccc tgaatgcctt    3560
tttgtgccag actgtcccaa gaatcctaat ttgtattcca tagaggtatt ttattttttaa    3620 tcctagagct tcttattgat ggatccttta gaattgccta cctaaaaggt aaactatact    3680
atccttataa atactgatca atcccagttc tcccccctaaa aatgaataca tagtaggact    3740
atagcaaatg tgtttgatgg gtaattctag actgggacta tggtacccct ttccagagtt    3800
ttaaaattca accttcatta cagacaaagt tttctcccag aaggaatgga ttgatagatt    3860
ttgattaaag taagggtgga aggaaatctg tagctggatt taccacaagt gacatctaga    3920
aactatagtt cacaggacag agcagagcca tggagaataa gcattgacta ccttgagttc    3980
tcctagtgag gagttctggt ataaaattta agattactac cagtaaccaa cttaaagcaa    4040 actataggg tccctaattt tggattttcc cttaagtgta agaaacaatg cttcaaatgt    4100
taagaaataa cagtctgggc aaagaacgca tattctatag gaagccaggt ttacaatagg    4160
taagaataaa ctgtattaag tagatgtaat gactagaaag ctgctttgct ccctatattg    4220
agaaattgtg gacatggtat gtgttatcca aagaacattg ggctagaaga tagatttcta    4280
tccttagctt tggcattatt gactggattg acttgaacaa gtcgcttaac ttctacaagc    4340
ttgtttcctt atttgtcaaa ttagattaca ctaggaaacg attctcgaac atgttttaac    4400
cttacaactc tttgttcaaa taaatctttc aatgaatccc caacataaaa aaaaaaaaa    4460 aaaaaaaaaa aaaaaa                                                    4476
```

<210> SEQ ID NO 2
<211> LENGTH: 934
<212> TYPE: PRT
<213> ORGANISM: Homo sapiens

<400> SEQUENCE: 2

```
Met Ala Ala Ser Arg Leu Asp Phe Gly Glu Val Glu Thr Phe Leu Asp
1               5                   10                  15

Arg His Pro Glu Leu Phe Glu Asp Tyr Leu Met Arg Lys Gly Lys Gln
            20                  25                  30

Glu Met Val Glu Lys Trp Leu Gln Arg His Ser Gln Gly Gln Gly Ala
        35                  40                  45

Leu Gly Pro Arg Pro Ser Leu Ala Gly Thr Ser Leu Ala His Ser
    50                  55                  60

Thr Cys Arg Gly Gly Ser Ser Val Gly Gly Thr Gly Pro Asn Gly
65                  70                  75                  80

Ser Ala His Ser Gln Pro Leu Pro Gly Gly Asp Cys Gly Gly Val
                85                  90                  95

Pro Leu Ser Pro Ser Trp Ala Gly Gly Ser Arg Gly Asp Gly Asn Leu
            100                 105                 110
```

```
Gln Arg Arg Ala Ser Gln Lys Glu Leu Arg Lys Ser Phe Ala Arg Ser
        115                 120                 125
Lys Ala Ile His Val Asn Arg Thr Tyr Asp Glu Gln Val Thr Ser Arg
130                 135                 140
Ala Gln Glu Pro Leu Ser Ser Val Arg Arg Ala Leu Leu Arg Lys
145                 150                 155                 160
Ala Ser Ser Leu Pro Pro Thr Thr Ala His Ile Leu Ser Ala Leu Leu
                165                 170                 175
Glu Ser Arg Val Asn Leu Pro Gln Tyr Pro Pro Thr Ala Ile Asp Tyr
                180                 185                 190
Lys Cys His Leu Lys Lys His Asn Glu Arg Gln Phe Phe Leu Glu Leu
                195                 200                 205
Val Lys Asp Ile Ser Asn Asp Leu Asp Leu Thr Ser Leu Ser Tyr Lys
210                 215                 220
Ile Leu Ile Phe Val Cys Leu Met Val Asp Ala Asp Arg Cys Ser Leu
225                 230                 235                 240
Phe Leu Val Glu Gly Ala Ala Gly Lys Lys Thr Leu Val Ser Lys
                245                 250                 255
Phe Phe Asp Val His Ala Gly Thr Pro Leu Leu Pro Cys Ser Ser Thr
                260                 265                 270
Glu Asn Ser Asn Glu Val Gln Val Pro Trp Gly Lys Gly Ile Ile Gly
                275                 280                 285
Tyr Val Gly Glu His Gly Glu Thr Val Asn Ile Pro Asp Ala Tyr Gln
                290                 295                 300
Asp Arg Arg Phe Asn Asp Glu Ile Asp Lys Leu Thr Gly Tyr Lys Thr
305                 310                 315                 320
Lys Ser Leu Leu Cys Met Pro Ile Arg Ser Ser Asp Gly Glu Ile Ile
                325                 330                 335
Gly Val Ala Gln Ala Ile Asn Lys Ile Pro Glu Gly Ala Pro Phe Thr
                340                 345                 350
Glu Asp Asp Glu Lys Val Met Gln Met Tyr Leu Pro Phe Cys Gly Ile
                355                 360                 365
Ala Ile Ser Asn Ala Gln Leu Phe Ala Ala Ser Arg Lys Glu Tyr Glu
370                 375                 380
Arg Ser Arg Ala Leu Leu Glu Val Val Asn Asp Leu Phe Glu Glu Gln
385                 390                 395                 400
Thr Asp Leu Glu Lys Ile Val Lys Lys Ile Met His Arg Ala Gln Thr
                405                 410                 415
Leu Leu Lys Cys Glu Arg Cys Ser Val Leu Leu Leu Glu Asp Ile Glu
                420                 425                 430
Ser Pro Val Val Lys Phe Thr Lys Ser Phe Glu Leu Met Ser Pro Lys
                435                 440                 445
Cys Ser Ala Asp Ala Glu Asn Ser Phe Lys Glu Ser Met Glu Lys Ser
                450                 455                 460
Ser Tyr Ser Asp Trp Leu Ile Asn Asn Ser Ile Ala Glu Leu Val Ala
465                 470                 475                 480
Ser Thr Gly Leu Pro Val Asn Ile Ser Asp Ala Tyr Gln Asp Pro Arg
                485                 490                 495
Phe Asp Ala Glu Ala Asp Gln Ile Ser Gly Phe His Ile Arg Ser Val
                500                 505                 510
Leu Cys Val Pro Ile Trp Asn Ser Asn His Gln Ile Ile Gly Val Ala
                515                 520                 525
Gln Val Leu Asn Arg Leu Asp Gly Lys Pro Phe Asp Asp Ala Asp Gln
                530                 535                 540
```

```
Arg Leu Phe Glu Ala Phe Val Ile Phe Cys Gly Leu Gly Ile Asn Asn
545                 550                 555                 560

Thr Ile Met Tyr Asp Gln Val Lys Lys Ser Trp Ala Lys Gln Ser Val
            565                 570                 575

Ala Leu Asp Val Leu Ser Tyr His Ala Thr Cys Ser Lys Ala Glu Val
        580                 585                 590

Asp Lys Phe Lys Ala Ala Asn Ile Pro Leu Val Ser Glu Leu Ala Ile
    595                 600                 605

Asp Asp Ile His Phe Asp Asp Phe Ser Leu Asp Val Asp Ala Met Ile
610                 615                 620

Thr Ala Ala Leu Arg Met Phe Met Glu Leu Gly Met Val Gln Lys Phe
625                 630                 635                 640

Lys Ile Asp Tyr Glu Thr Leu Cys Arg Trp Leu Leu Thr Val Arg Lys
            645                 650                 655

Asn Tyr Arg Met Val Leu Tyr His Asn Trp Arg His Ala Phe Asn Val
        660                 665                 670

Cys Gln Leu Met Phe Ala Met Leu Thr Thr Ala Gly Phe Gln Asp Ile
    675                 680                 685

Leu Thr Glu Val Glu Ile Leu Ala Val Ile Val Gly Cys Leu Cys His
690                 695                 700

Asp Leu Asp His Arg Gly Thr Asn Asn Ala Phe Gln Ala Lys Ser Gly
705                 710                 715                 720

Ser Ala Leu Ala Gln Leu Tyr Gly Thr Ser Ala Thr Leu Glu His His
            725                 730                 735

His Phe Asn His Ala Val Met Ile Leu Gln Ser Glu Gly His Asn Ile
        740                 745                 750

Phe Ala Asn Leu Ser Ser Lys Glu Tyr Ser Asp Leu Met Gln Leu Leu
    755                 760                 765

Lys Gln Ser Ile Leu Ala Thr Asp Leu Thr Leu Tyr Phe Glu Arg Arg
770                 775                 780

Thr Glu Phe Phe Glu Leu Val Ser Lys Gly Glu Tyr Asp Trp Asn Ile
785                 790                 795                 800

Lys Asn His Arg Asp Ile Phe Arg Ser Met Leu Met Thr Ala Cys Asp
            805                 810                 815

Leu Gly Ala Val Thr Lys Pro Trp Glu Ile Ser Arg Gln Val Ala Glu
        820                 825                 830

Leu Val Thr Ser Glu Phe Phe Glu Gln Gly Asp Arg Glu Arg Leu Glu
    835                 840                 845

Leu Lys Leu Thr Pro Ser Ala Ile Phe Asp Arg Asn Arg Lys Asp Glu
850                 855                 860

Leu Pro Arg Leu Gln Leu Glu Trp Ile Asp Ser Ile Cys Met Pro Leu
865                 870                 875                 880

Tyr Gln Ala Leu Val Lys Val Asn Val Lys Leu Lys Pro Met Leu Asp
            885                 890                 895

Ser Val Ala Thr Asn Arg Ser Lys Trp Glu Glu Leu His Gln Lys Arg
        900                 905                 910

Leu Leu Ala Ser Thr Ala Ser Ser Ser Pro Ala Ser Val Met Val
    915                 920                 925

Ala Lys Glu Asp Arg Asn
    930
```

<210> SEQ ID NO 3
<211> LENGTH: 3507
<212> TYPE: DNA

```
<213> ORGANISM: Homo sapiens
<220> FEATURE:
<221> NAME/KEY: CDS
<222> LOCATION: (100)..(2151)

<400> SEQUENCE: 3
cgcttgcagc ccagggcgtg aggtgctctt tctggatcgc cagcctcgaa gttgaggcgt      60
ggactctggc caggtggctg ttccagagca acatgggag atg ctg aag cag gca       114
                                           Met Leu Lys Gln Ala
                                             1               5 aga aga cct tta ttc aga aat gtg ctc agt gcc aca cag tgg aaa aag      162
Arg Arg Pro Leu Phe Arg Asn Val Leu Ser Ala Thr Gln Trp Lys Lys
             10                  15                  20 gtg aaa atc aca aga ctg gtc caa atc tct ggg gcc tct ttg gct gaa      210
Val Lys Ile Thr Arg Leu Val Gln Ile Ser Gly Ala Ser Leu Ala Glu
         25                  30                  35 aaa cag gaa aag cac cag gat ttt ctt ata cag agg caa aca aaa aca      258
Lys Gln Glu Lys His Gln Asp Phe Leu Ile Gln Arg Gln Thr Lys Thr
     40                  45                  50 aag gat cga cga ttc aat gat gaa atc gac aag cta act gga tac aag      306
Lys Asp Arg Arg Phe Asn Asp Glu Ile Asp Lys Leu Thr Gly Tyr Lys
 55                  60                  65 aca aaa tca tta ttg tgc atg cct atc cga agc agt gat ggt gag att      354
Thr Lys Ser Leu Leu Cys Met Pro Ile Arg Ser Ser Asp Gly Glu Ile
 70                  75                  80                  85 att ggt gtg gcc caa gcg ata aat aag att cct gaa gga gct cca ttt      402
Ile Gly Val Ala Gln Ala Ile Asn Lys Ile Pro Glu Gly Ala Pro Phe
             90                  95                 100 act gaa gat gat gaa aaa gtt atg cag atg tat ctt cca ttt tgt gga      450
Thr Glu Asp Asp Glu Lys Val Met Gln Met Tyr Leu Pro Phe Cys Gly
        105                 110                 115 atc gcc ata tct aac gct cag ctc ttt gct gcc tca agg aaa gaa tat      498
Ile Ala Ile Ser Asn Ala Gln Leu Phe Ala Ala Ser Arg Lys Glu Tyr
    120                 125                 130 gaa aga agc aga gct ttg cta gag gtg gtt aat gac ctc ttt gaa gaa      546
Glu Arg Ser Arg Ala Leu Leu Glu Val Val Asn Asp Leu Phe Glu Glu
135                 140                 145 cag act gac ctg gag aaa att gtc aag aaa ata atg cat cgg gcc caa      594
Gln Thr Asp Leu Glu Lys Ile Val Lys Lys Ile Met His Arg Ala Gln
150                 155                 160                 165 act ctg ctg aaa tgt gag cgc tgt tct gtt tta ctc cta gag gac atc      642
Thr Leu Leu Lys Cys Glu Arg Cys Ser Val Leu Leu Leu Glu Asp Ile
            170                 175                 180 gaa tca cca gtg gtg aaa ttt acc aaa tcc ttt gaa ttg atg tcc cca      690
Glu Ser Pro Val Val Lys Phe Thr Lys Ser Phe Glu Leu Met Ser Pro
        185                 190                 195 aag tgc agt gct gat gct gag aac agt ttc aaa gaa agc atg gag aaa      738
Lys Cys Ser Ala Asp Ala Glu Asn Ser Phe Lys Glu Ser Met Glu Lys
    200                 205                 210 tca tca tac tcc gac tgg cta ata aat aac agc att gct gag ctg gtt      786
Ser Ser Tyr Ser Asp Trp Leu Ile Asn Asn Ser Ile Ala Glu Leu Val
215                 220                 225 gct tca aca ggc ctt cca gtg aac atc agt gat gcc tac cag gat ccg      834
Ala Ser Thr Gly Leu Pro Val Asn Ile Ser Asp Ala Tyr Gln Asp Pro
230                 235                 240                 245 cgc ttt gat gca gag gca gac cag ata tct ggt ttt cac ata aga tct      882
Arg Phe Asp Ala Glu Ala Asp Gln Ile Ser Gly Phe His Ile Arg Ser
            250                 255                 260 gtt ctt tgt gtc cct att tgg aat agc aac cac caa ata att gga gtg      930
Val Leu Cys Val Pro Ile Trp Asn Ser Asn His Gln Ile Ile Gly Val
        265                 270                 275
```

```
gct caa gtg tta aac aga ctt gat ggg aaa cct ttt gat gat gca gat      978
Ala Gln Val Leu Asn Arg Leu Asp Gly Lys Pro Phe Asp Asp Ala Asp
        280                 285                 290 caa cga ctt ttt gag gct ttt gtc atc ttt tgt gga ctt ggc atc aac     1026
Gln Arg Leu Phe Glu Ala Phe Val Ile Phe Cys Gly Leu Gly Ile Asn
    295                 300                 305 aac aca att atg tat gat caa gtg aag aag tcc tgg gcc aag cag tct     1074
Asn Thr Ile Met Tyr Asp Gln Val Lys Lys Ser Trp Ala Lys Gln Ser
310                 315                 320                 325 gtg gct ctt gat gtg cta tca tac cat gca aca tgt tca aaa gct gaa     1122
Val Ala Leu Asp Val Leu Ser Tyr His Ala Thr Cys Ser Lys Ala Glu
                330                 335                 340 gtt gac aag ttt aag gca gcc aac atc cct ctg gtc tca gaa ctt gcc     1170
Val Asp Lys Phe Lys Ala Ala Asn Ile Pro Leu Val Ser Glu Leu Ala
            345                 350                 355 atc gat gac att cat ttt gat gac ttt tct ctc gac gtt gat gcc atg     1218
Ile Asp Asp Ile His Phe Asp Asp Phe Ser Leu Asp Val Asp Ala Met
        360                 365                 370 atc aca gct gct ctc cgg atg ttc atg gag ctg ggg atg gta cag aaa     1266
Ile Thr Ala Ala Leu Arg Met Phe Met Glu Leu Gly Met Val Gln Lys
    375                 380                 385 ttt aaa att gac tat gag aca ctg tgt agg tgg ctt ttg aca gtg agg     1314
Phe Lys Ile Asp Tyr Glu Thr Leu Cys Arg Trp Leu Leu Thr Val Arg
390                 395                 400                 405 aaa aac tat cgg atg gtt cta tac cac aac tgg aga cat gcc ttc aac     1362
Lys Asn Tyr Arg Met Val Leu Tyr His Asn Trp Arg His Ala Phe Asn
                410                 415                 420 gtg tgt cag ctg atg ttc gcg atg tta acc act gct ggg ttt caa gac     1410
Val Cys Gln Leu Met Phe Ala Met Leu Thr Thr Ala Gly Phe Gln Asp
            425                 430                 435 att ctg acc gag gtg gaa att tta gcg gtg att gtg gga tgc ctg tgt     1458
Ile Leu Thr Glu Val Glu Ile Leu Ala Val Ile Val Gly Cys Leu Cys
        440                 445                 450 cat gac ctc gac cac agg gga acc aac aat gcc ttc caa gct aag agt     1506
His Asp Leu Asp His Arg Gly Thr Asn Asn Ala Phe Gln Ala Lys Ser
    455                 460                 465 ggc tct gcc ctg gcc caa ctc tat gga acc tct gct acc ttg gag cat     1554
Gly Ser Ala Leu Ala Gln Leu Tyr Gly Thr Ser Ala Thr Leu Glu His
470                 475                 480                 485 cac cat ttc aac cac gcc gtg atg atc ctt caa agt gag ggt cac aat     1602
His His Phe Asn His Ala Val Met Ile Leu Gln Ser Glu Gly His Asn
                490                 495                 500 atc ttt gct aac ctg tcc tcc aag gaa tat agt gac ctt atg cag ctt     1650
Ile Phe Ala Asn Leu Ser Ser Lys Glu Tyr Ser Asp Leu Met Gln Leu
            505                 510                 515 ttg aag cag tca ata ttg gca aca gac ctc acg ctg tac ttt gag agg     1698
Leu Lys Gln Ser Ile Leu Ala Thr Asp Leu Thr Leu Tyr Phe Glu Arg
        520                 525                 530 aga act gaa ttc ttt gaa ctt gtc agt aaa gga gaa tac gat tgg aac     1746
Arg Thr Glu Phe Phe Glu Leu Val Ser Lys Gly Glu Tyr Asp Trp Asn
    535                 540                 545 atc aaa aac cat cgt gat ata ttt cga tca atg tta atg aca gcc tgt     1794
Ile Lys Asn His Arg Asp Ile Phe Arg Ser Met Leu Met Thr Ala Cys
550                 555                 560                 565 gac ctt gga gcc gtg acc aaa ccg tgg gag atc tcc aga cag gtg gca     1842
Asp Leu Gly Ala Val Thr Lys Pro Trp Glu Ile Ser Arg Gln Val Ala
                570                 575                 580 gaa ctt gta acc agt gag ttc ttc gaa caa gga gat cgg gag aga tta     1890
Glu Leu Val Thr Ser Glu Phe Phe Glu Gln Gly Asp Arg Glu Arg Leu
            585                 590                 595
```

```
gag  ctc  aaa  ctc  act  cct  tca  gca  att  ttt  gat  cgg  aac  cgg  aag  gat      1938
Glu  Leu  Lys  Leu  Thr  Pro  Ser  Ala  Ile  Phe  Asp  Arg  Asn  Arg  Lys  Asp
          600                 605                      610 gaa  ctg  cct  cgg  ttg  caa  ctg  gag  tgg  att  gat  agc  atc  tgc  atg  cct      1986
Glu  Leu  Pro  Arg  Leu  Gln  Leu  Glu  Trp  Ile  Asp  Ser  Ile  Cys  Met  Pro
     615                      620                      625 ttg  tat  cag  gca  ctg  gtg  aag  gtc  aac  gtg  aaa  ctg  aag  ccg  atg  cta      2034
Leu  Tyr  Gln  Ala  Leu  Val  Lys  Val  Asn  Val  Lys  Leu  Lys  Pro  Met  Leu
630                      635                      640                      645 gat  tca  gta  gct  aca  aac  aga  agt  aag  tgg  gaa  gag  cta  cac  caa  aaa      2082
Asp  Ser  Val  Ala  Thr  Asn  Arg  Ser  Lys  Trp  Glu  Glu  Leu  His  Gln  Lys
               650                      655                      660 cga  ctg  ctg  gcc  tca  act  gcc  tca  tcc  tcc  tcc  cct  gcc  agt  gtt  atg      2130
Arg  Leu  Leu  Ala  Ser  Thr  Ala  Ser  Ser  Ser  Ser  Pro  Ala  Ser  Val  Met
          665                      670                      675 gta  gcc  aag  gaa  gac  agg  aac  taaacctcca ggtcagctgc agctgcaaaa                  2181
Val  Ala  Lys  Glu  Asp  Arg  Asn
          680
```
tgactacagc ctgaagggcc attttcagtc cagcaatgtc atccttttgt tcttttagct     2241
cagaaagacc taacatctca aggatgcact gggaaccatg cctgggcttt caccttgaag     2301
catggtcagc agcagagaga gcaacgggaa ggacaaagaa agaggtgggg cagggagcac     2361
accccaggac cctcactttt ccctaatgaa cacgcatggg ctgaaatgaa ggctctgggt     2421
aggggactgt tttggatcca aggacctgtg gacagtcggc ctacttactc tgagctgagg     2481
gaacactgaa cagtaaaagc gtcattagcg ctgcttcatt ttgtataggg cttttctgtt     2541
tgttacaagc caaacattgc ctgtctttgc ttcccgtccc tgaatgcctt tttgtgccag     2601
actgtcccaa gaatcctaat ttgtattcca tagaggtatt ttatttttaa tcctagagct     2661
tcttattgat ggatccttta gaattgccta cctaaaaggt aaactatact atccttataa     2721
atactgatca atcccagttc tcccctaaa aatgaataca tagtaggact atagcaaatg      2781
tgtttgatgg gtaattctag actgggacta tggtacccct tccagagttt ttaaaattca     2841
accttcatta cagacaaagt tttctcccag aaggaatgga ttgatagatt ttgattaaag     2901
taagggtgga aggaaatctg tagctggatt taccacaagt gacatctaga aactatagtt     2961
cacaggacag agcagagcca tggagaataa gcattgacta ccttgagttc tcctagtgag     3021
gagttctggt ataaaattta agattactac cagtaaccaa cttaaagcaa actataggg      3081 tccctaattt tggatttttc cttaagtgta agaaacaatg cttcaaatgt taagaaataa     3141
cagtctgggc aaagaacgca tattctatag gaagccaggt ttacaatagg taagaataaa     3201
ctgtattaag tagatgtaat gactagaaag ctgctttgct ccctatattg agaaattgtg     3261
gacatggtat gtgttatcca agaacattg  ggctagaaga tagatttcta tccttagctt     3321
tggcattatt gactggattg acttgaacaa gtcgcttaac ttctacaagc ttgtttcctt     3381
atttgtcaaa ttagattaca ctaggaaacg attctcgaac atgttttaac cttacaactc     3441
tttgttcaaa taaatctttc aatgaatccc caacataaaa aaaaaaaaaa aaaaaaaaaa     3501
aaaaaa                                                                3507

<210> SEQ ID NO 4
<211> LENGTH: 684
<212> TYPE: PRT
<213> ORGANISM: Homo sapiens

<400> SEQUENCE: 4

Met Leu Lys Gln Ala Arg Arg Pro Leu Phe Arg Asn Val Leu Ser Ala

```
  1               5                  10                 15
Thr Gln Trp Lys Lys Val Lys Ile Thr Arg Leu Val Gln Ile Ser Gly
             20                  25                  30

Ala Ser Leu Ala Glu Lys Gln Glu Lys His Gln Asp Phe Leu Ile Gln
             35                  40                  45

Arg Gln Thr Lys Thr Lys Asp Arg Arg Phe Asn Asp Glu Ile Asp Lys
             50                  55                  60

Leu Thr Gly Tyr Lys Thr Lys Ser Leu Leu Cys Met Pro Ile Arg Ser
 65                  70                  75                  80

Ser Asp Gly Glu Ile Ile Gly Val Ala Gln Ala Ile Asn Lys Ile Pro
                 85                  90                  95

Glu Gly Ala Pro Phe Thr Glu Asp Glu Lys Val Met Gln Met Tyr
                100                 105                 110

Leu Pro Phe Cys Gly Ile Ala Ile Ser Asn Ala Gln Leu Phe Ala Ala
            115                 120                 125

Ser Arg Lys Glu Tyr Glu Arg Ser Arg Ala Leu Leu Glu Val Val Asn
            130                 135                 140

Asp Leu Phe Glu Glu Gln Thr Asp Leu Glu Lys Ile Val Lys Lys Ile
145                 150                 155                 160

Met His Arg Ala Gln Thr Leu Leu Lys Cys Glu Arg Cys Ser Val Leu
                165                 170                 175

Leu Leu Glu Asp Ile Glu Ser Pro Val Val Lys Phe Thr Lys Ser Phe
            180                 185                 190

Glu Leu Met Ser Pro Lys Cys Ser Ala Asp Ala Glu Asn Ser Phe Lys
            195                 200                 205

Glu Ser Met Glu Lys Ser Ser Tyr Ser Asp Trp Leu Ile Asn Asn Ser
210                 215                 220

Ile Ala Glu Leu Val Ala Ser Thr Gly Leu Pro Val Asn Ile Ser Asp
225                 230                 235                 240

Ala Tyr Gln Asp Pro Arg Phe Asp Ala Glu Ala Asp Gln Ile Ser Gly
                245                 250                 255

Phe His Ile Arg Ser Val Leu Cys Val Pro Ile Trp Asn Ser Asn His
            260                 265                 270

Gln Ile Ile Gly Val Ala Gln Val Leu Asn Arg Leu Asp Gly Lys Pro
            275                 280                 285

Phe Asp Asp Ala Asp Gln Arg Leu Phe Glu Ala Phe Val Ile Phe Cys
            290                 295                 300

Gly Leu Gly Ile Asn Asn Thr Ile Met Tyr Asp Gln Val Lys Lys Ser
305                 310                 315                 320

Trp Ala Lys Gln Ser Val Ala Leu Asp Val Leu Ser Tyr His Ala Thr
                325                 330                 335

Cys Ser Lys Ala Glu Val Asp Lys Phe Lys Ala Ala Asn Ile Pro Leu
            340                 345                 350

Val Ser Glu Leu Ala Ile Asp Asp Ile His Phe Asp Phe Ser Leu
            355                 360                 365

Asp Val Asp Ala Met Ile Thr Ala Ala Leu Arg Met Phe Met Glu Leu
            370                 375                 380

Gly Met Val Gln Lys Phe Lys Ile Asp Tyr Glu Thr Leu Cys Arg Trp
385                 390                 395                 400

Leu Leu Thr Val Arg Lys Asn Tyr Arg Met Val Leu Tyr His Asn Trp
                405                 410                 415

Arg His Ala Phe Asn Val Cys Gln Leu Met Phe Ala Met Leu Thr Thr
            420                 425                 430
```

```
Ala Gly Phe Gln Asp Ile Leu Thr Glu Val Glu Ile Leu Ala Val Ile
            435                 440                 445

Val Gly Cys Leu Cys His Asp Leu Asp His Arg Gly Thr Asn Asn Ala
450                 455                 460

Phe Gln Ala Lys Ser Gly Ser Ala Leu Ala Gln Leu Tyr Gly Thr Ser
465                 470                 475                 480

Ala Thr Leu Glu His His His Phe Asn His Ala Val Met Ile Leu Gln
            485                 490                 495

Ser Glu Gly His Asn Ile Phe Ala Asn Leu Ser Ser Lys Glu Tyr Ser
            500                 505                 510

Asp Leu Met Gln Leu Leu Lys Gln Ser Ile Leu Ala Thr Asp Leu Thr
            515                 520                 525

Leu Tyr Phe Glu Arg Arg Thr Glu Phe Phe Glu Leu Val Ser Lys Gly
            530                 535                 540

Glu Tyr Asp Trp Asn Ile Lys Asn His Arg Asp Ile Phe Arg Ser Met
545                 550                 555                 560

Leu Met Thr Ala Cys Asp Leu Gly Ala Val Thr Lys Pro Trp Glu Ile
                565                 570                 575

Ser Arg Gln Val Ala Glu Leu Val Thr Ser Glu Phe Phe Glu Gln Gly
            580                 585                 590

Asp Arg Glu Arg Leu Glu Leu Lys Leu Thr Pro Ser Ala Ile Phe Asp
            595                 600                 605

Arg Asn Arg Lys Asp Glu Leu Pro Arg Leu Gln Leu Glu Trp Ile Asp
610                 615                 620

Ser Ile Cys Met Pro Leu Tyr Gln Ala Leu Val Lys Val Asn Val Lys
625                 630                 635                 640

Leu Lys Pro Met Leu Asp Ser Val Ala Thr Asn Arg Ser Lys Trp Glu
                645                 650                 655

Glu Leu His Gln Lys Arg Leu Leu Ala Ser Thr Ala Ser Ser Ser Ser
            660                 665                 670

Pro Ala Ser Val Met Val Ala Lys Glu Asp Arg Asn
            675                 680

<210> SEQ ID NO 5
<211> LENGTH: 3492
<212> TYPE: DNA
<213> ORGANISM: Rat
<220> FEATURE:
<221> NAME/KEY: CDS
<222> LOCATION: (241)..(2295)

<400> SEQUENCE: 5
gcggggagcg aggatggagc ccgccatcag ctggtgcatg atccggcctg taagcggagt      60
cctcgggcac agcagtcgcg ccttaaatct tggcctcact gcatcagtgg accagggtg     120 gctcagggca cgcgctgctg tgatcgtgaaa acaaagaata gggaaaccaa gtccaggttt    180
gcaaatctga gactttttt ggttggtgat ttaaggtttt attgccgagc aaaatgggag     240 atg ctg aag cag gca aga aga ttt tca ttc aga aat gtg cgc agt gcc     288
Met Leu Lys Gln Ala Arg Arg Phe Ser Phe Arg Asn Val Arg Ser Ala
1               5                   10                  15 aca cag tgg aga aag gtg gga agc aca aga cag ggc caa atc tct ggg     336
Thr Gln Trp Arg Lys Val Gly Ser Thr Arg Gln Gly Gln Ile Ser Gly
            20                  25                  30 gcc ttt ttg gcc gaa aga ctg gac aag cac cag gat ttt ctt aca cgg     384
Ala Phe Leu Ala Glu Arg Leu Asp Lys His Gln Asp Phe Leu Thr Arg
        35                  40                  45 atg caa aca aga aca aag gac cga aga ttc aat gat gaa att gac aag     432
```

```
                Met Gln Thr Arg Thr Lys Asp Arg Arg Phe Asn Asp Glu Ile Asp Lys
                    50                  55                  60 ctg act gga tac aag aca aaa tca cta ttg tgc atg cct atc cgg aac      480
Leu Thr Gly Tyr Lys Thr Lys Ser Leu Leu Cys Met Pro Ile Arg Asn
65                  70                  75                  80 agt gac ggt gag att atc ggt gtg gcc cag gcg ata aat aag gtt cct      528
Ser Asp Gly Glu Ile Ile Gly Val Ala Gln Ala Ile Asn Lys Val Pro
                85                  90                  95 gag ggt gct cca ttt aca gaa gac gaa aaa gtt atg cag atg tat          576
Glu Gly Ala Pro Phe Thr Glu Asp Glu Lys Val Met Gln Met Tyr
            100                 105                 110 ctt cca ttc tgt ggc atc gcc ata tct aat gct cag ctc ttc gcc gcc      624
Leu Pro Phe Cys Gly Ile Ala Ile Ser Asn Ala Gln Leu Phe Ala Ala
            115                 120                 125 tcg agg aaa gaa tat gaa aga agt agg gcc ttg ctg gag gtg gtc aat      672
Ser Arg Lys Glu Tyr Glu Arg Ser Arg Ala Leu Leu Glu Val Val Asn
        130                 135                 140 gac ctc ttt gaa gaa cag act gac ctg gaa aag att gtc aag aaa ata      720
Asp Leu Phe Glu Glu Gln Thr Asp Leu Glu Lys Ile Val Lys Lys Ile
145                 150                 155                 160 atg cat cgg gcc caa act ctg ttg aaa tgt gaa cgc tgt tcc gtt tta      768
Met His Arg Ala Gln Thr Leu Leu Lys Cys Glu Arg Cys Ser Val Leu
                165                 170                 175 ctt cta gaa gac att gaa tca cca gtg gtg aag ttt acc aaa tcc ttt      816
Leu Leu Glu Asp Ile Glu Ser Pro Val Val Lys Phe Thr Lys Ser Phe
            180                 185                 190 gaa ctg atg tcc cca aag tgc agt gcg gac gcg gag aac agt ttc aaa      864
Glu Leu Met Ser Pro Lys Cys Ser Ala Asp Ala Glu Asn Ser Phe Lys
        195                 200                 205 gaa agt gtg gag aag tca tct tac tcc gac tgg ctg ata aat aac agt      912
Glu Ser Val Glu Lys Ser Ser Tyr Ser Asp Trp Leu Ile Asn Asn Ser
210                 215                 220 atc gct gag ctg gtt gct tcg aca ggc ctt cct gtg aat gtc agc gat      960
Ile Ala Glu Leu Val Ala Ser Thr Gly Leu Pro Val Asn Val Ser Asp
225                 230                 235                 240 gcc tac cag gac cca cgc ttt gac gct gag gct gac cag ata tct ggc     1008
Ala Tyr Gln Asp Pro Arg Phe Asp Ala Glu Ala Asp Gln Ile Ser Gly
                245                 250                 255 ttt cat ata aga tct gtt ctc tgt gtc cct att tgg aac agc aac cac     1056
Phe His Ile Arg Ser Val Leu Cys Val Pro Ile Trp Asn Ser Asn His
            260                 265                 270 caa ata ata ggg gtc gct caa gtg ctg aac aga ctc gat ggg aaa cct     1104
Gln Ile Ile Gly Val Ala Gln Val Leu Asn Arg Leu Asp Gly Lys Pro
        275                 280                 285 ttt gat gat gct gac caa agg ctt ttt gag gcc ttt gtc atc ttt tgt     1152
Phe Asp Asp Ala Asp Gln Arg Leu Phe Glu Ala Phe Val Ile Phe Cys
        290                 295                 300 ggc ctt ggt att aac aac acg att atg tat gac caa gtg aag aag tcc     1200
Gly Leu Gly Ile Asn Asn Thr Ile Met Tyr Asp Gln Val Lys Lys Ser
305                 310                 315                 320 tgg gcc aag cag tcc gtg gct ctt gat gtg ctg tcc tac cac gcc acg     1248
Trp Ala Lys Gln Ser Val Ala Leu Asp Val Leu Ser Tyr His Ala Thr
                325                 330                 335 tgt tcc aag gct gaa gtt gac aag ttt aag gca gcc aac atc ccc ctg     1296
Cys Ser Lys Ala Glu Val Asp Lys Phe Lys Ala Ala Asn Ile Pro Leu
            340                 345                 350 gtg tcg gaa ctg gcc atc gat gac atc cat ttt gat gac ttt tcc ctt     1344
Val Ser Glu Leu Ala Ile Asp Asp Ile His Phe Asp Asp Phe Ser Leu
        355                 360                 365 gat gtt gat gcc atg atc aca gcc gct cta cgg atg ttc atg gag ctg     1392
```

-continued

```
               Asp Val Asp Ala Met Ile Thr Ala Ala Leu Arg Met Phe Met Glu Leu
               370                 375                 380 ggg atg gta cag aaa ttt aaa atc gac tat gag acc ctg tgc agg tgg        1440
Gly Met Val Gln Lys Phe Lys Ile Asp Tyr Glu Thr Leu Cys Arg Trp
385                 390                 395                 400 ctt ctg aca gta agg aaa aac tat cgg atg gtt ctc tac cac aac tgg        1488
Leu Leu Thr Val Arg Lys Asn Tyr Arg Met Val Leu Tyr His Asn Trp
                405                 410                 415 aga cat gcc ttc aac gtg tgc cag ctg atg ttt gcc atg cta act act        1536
Arg His Ala Phe Asn Val Cys Gln Leu Met Phe Ala Met Leu Thr Thr
            420                 425                 430 gct ggg ttt caa gag att ctg acc gag gtg gaa att tta gcg gtg att        1584
Ala Gly Phe Gln Glu Ile Leu Thr Glu Val Glu Ile Leu Ala Val Ile
        435                 440                 445 gtg gga tgc ctg tgt cat gac ctc gac cac agg gga acc aac aat gcc        1632
Val Gly Cys Leu Cys His Asp Leu Asp His Arg Gly Thr Asn Asn Ala
    450                 455                 460 ttc caa gct aag agt gac tct gca ctg gcc cag ctc tat ggg acc tca        1680
Phe Gln Ala Lys Ser Asp Ser Ala Leu Ala Gln Leu Tyr Gly Thr Ser
465                 470                 475                 480 gcg acc tta gag cat cac cac ttt aac cac gcc gtg atg atc ctt cag        1728
Ala Thr Leu Glu His His His Phe Asn His Ala Val Met Ile Leu Gln
                485                 490                 495 agt gag ggt cac aac atc ttt gct aat ttg tcc tcc aag gaa tac agc        1776
Ser Glu Gly His Asn Ile Phe Ala Asn Leu Ser Ser Lys Glu Tyr Ser
            500                 505                 510 gac ctc atg cag ctc ctg aag cag tcg ata cta gcc act gac ctc acg        1824
Asp Leu Met Gln Leu Leu Lys Gln Ser Ile Leu Ala Thr Asp Leu Thr
        515                 520                 525 ctg tac ttc gag aga aga act gag ttc ttc gag ctt gtc agt aaa gga        1872
Leu Tyr Phe Glu Arg Arg Thr Glu Phe Phe Glu Leu Val Ser Lys Gly
    530                 535                 540 gcc tat gat tgg agc atc aca agt cac cgc gat gtg ttt cga tca atg        1920
Ala Tyr Asp Trp Ser Ile Thr Ser His Arg Asp Val Phe Arg Ser Met
545                 550                 555                 560 tta atg aca gct tgt gac ctt gga gcc gtg acc aaa ccg tgg gag atc        1968
Leu Met Thr Ala Cys Asp Leu Gly Ala Val Thr Lys Pro Trp Glu Ile
                565                 570                 575 tcc aga cag gtg gct gaa ctt gtc acc agc gag ttc ttc gaa caa gga        2016
Ser Arg Gln Val Ala Glu Leu Val Thr Ser Glu Phe Phe Glu Gln Gly
            580                 585                 590 gat cgg gag agg tcg gaa ctc aag ctc acc ccc tct gct att ttt gac        2064
Asp Arg Glu Arg Ser Glu Leu Lys Leu Thr Pro Ser Ala Ile Phe Asp
        595                 600                 605 cgg aac cgg aaa gat gag ctg cct cgg ctg caa ctg gag tgg att gac        2112
Arg Asn Arg Lys Asp Glu Leu Pro Arg Leu Gln Leu Glu Trp Ile Asp
    610                 615                 620 agc atc tgc atg cct ttg tat cag gcc ttg gtg aaa gtc aat gca aaa        2160
Ser Ile Cys Met Pro Leu Tyr Gln Ala Leu Val Lys Val Asn Ala Lys
625                 630                 635                 640 ctg aag ccg atg ctg gac tca gtg gcc gcc aac cgc agg aag tgg gaa        2208
Leu Lys Pro Met Leu Asp Ser Val Ala Ala Asn Arg Arg Lys Trp Glu
                645                 650                 655 gag ttg cac caa aaa aga cta cag gtc tct gct gcc tcc cca gtc cct        2256
Glu Leu His Gln Lys Arg Leu Gln Val Ser Ala Ala Ser Pro Val Pro
            660                 665                 670 tcc agt ccc agc cca gcg gtg gcc gga gag gac aga ctg taaaccaccc         2305
Ser Ser Pro Ser Pro Ala Val Ala Gly Glu Asp Arg Leu
        675                 680                 685 agagctgctg cgccaccctg tggcctggag gaccctctgc atcctgaact atctgctttg      2365
```

-continued

```
gttgaatagc atcaccctct tcgttcagct cggacagtcc taaagctttg actggatcag    2425
gaagcacaca aggaagtgtg cttggcggca gagaaacgga aggatgaaga gaatacgacc    2485
ctcaactttg tcatgaaccc atgctgctgg atttggatcc gtggacctga aggccatcac    2545
cccactcgtg ctgagttgag aggacaccgt tgtaaaagtg tcactatggc tgcttcctgt    2605
atggcacttt tctgttatga gcatttcctt tctgtgcagc ctctccggag caggctccag    2665
ccggtcccaa gaatgcagat ttgcattcta ggtgttttgt ttctaatcta ctgcttcttt    2725
gtaatgcacc agaccttcg tctcctttgc tagtggataa gcctgctccc tttattagag    2785
ccaggtaacc ccaatcttgc ttgccacagt agtaatatag tgtgtttgtc taattggtgt    2845
tacacaggag ctgtaactct gcagtgagat agatcatggt tcagcttttt aattcagcct    2905
ttgttgcaaa caaagccttt ttctaggggg aaacagatta ataattttat taaagcaaag    2965
gtgaaaagga atctaaggcc acatgtacaa gtgacatgta tgaacaccag aaatgcttcc    3025
aacaaagaaa tatttcacag gtgcagagga accctgtgac cagtcgtgga atagtttgag    3085
gtgaagggga tgaaggtttg gggataaaat ttaaggaacc ctgattttac attttccctt    3145
acatgtaaaa aagaatgttc tagaaaggcc aggaaataac acctgcacaa cctatatcca    3205
gtaagaagtc agatctacag cacgtgaaaa cagtttaaaa gaggtatgct cactagaaag    3265
ctgcctgaga cactaaggac aggatctgtc ttacccaaag aacattgggc ttcctgtccc    3325
tcactttgca ttactagttg agtgagtttg gacctagatt tctctgtgtc aagcgagatt    3385
acactaggaa tttatttgca gtaatcttag cattaaaatc ttttgtccaa ataaacttcc    3445
aaggattccc cagggcacaa ggaaaaaaaa aaaaaaaaa aaaaaaa                  3492
```

```
<210> SEQ ID NO 6
<211> LENGTH: 685
<212> TYPE: PRT
<213> ORGANISM: Rat

<400> SEQUENCE: 6

Met Leu Lys Gln Ala Arg Arg Phe Ser Phe Arg Asn Val Arg Ser Ala
1               5                   10                  15

Thr Gln Trp Arg Lys Val Gly Ser Thr Arg Gln Gly Gln Ile Ser Gly
            20                  25                  30

Ala Phe Leu Ala Glu Arg Leu Asp Lys His Gln Asp Phe Leu Thr Arg
        35                  40                  45

Met Gln Thr Arg Thr Lys Asp Arg Arg Phe Asn Asp Glu Ile Asp Lys
    50                  55                  60

Leu Thr Gly Tyr Lys Thr Lys Ser Leu Leu Cys Met Pro Ile Arg Asn
65                  70                  75                  80

Ser Asp Gly Glu Ile Ile Gly Val Ala Gln Ala Ile Asn Lys Val Pro
                85                  90                  95

Glu Gly Ala Pro Phe Thr Glu Asp Asp Glu Lys Val Met Gln Met Tyr
            100                 105                 110

Leu Pro Phe Cys Gly Ile Ala Ile Ser Asn Ala Gln Leu Phe Ala Ala
        115                 120                 125

Ser Arg Lys Glu Tyr Glu Arg Ser Arg Ala Leu Leu Glu Val Val Asn
    130                 135                 140

Asp Leu Phe Glu Glu Gln Thr Asp Leu Glu Lys Ile Val Lys Lys Ile
145                 150                 155                 160

Met His Arg Ala Gln Thr Leu Leu Lys Cys Glu Arg Cys Ser Val Leu
                165                 170                 175
```

-continued

```
Leu Leu Glu Asp Ile Glu Ser Pro Val Val Lys Phe Thr Lys Ser Phe
            180                 185                 190

Glu Leu Met Ser Pro Lys Cys Ser Ala Asp Ala Glu Asn Ser Phe Lys
        195                 200                 205

Glu Ser Val Glu Lys Ser Ser Tyr Ser Asp Trp Leu Ile Asn Asn Ser
    210                 215                 220

Ile Ala Glu Leu Val Ala Ser Thr Gly Leu Pro Val Asn Val Ser Asp
225                 230                 235                 240

Ala Tyr Gln Asp Pro Arg Phe Asp Ala Glu Ala Asp Gln Ile Ser Gly
                245                 250                 255

Phe His Ile Arg Ser Val Leu Cys Val Pro Ile Trp Asn Ser Asn His
            260                 265                 270

Gln Ile Ile Gly Val Ala Gln Val Leu Asn Arg Leu Asp Gly Lys Pro
        275                 280                 285

Phe Asp Asp Ala Asp Gln Arg Leu Phe Glu Ala Phe Val Ile Phe Cys
    290                 295                 300

Gly Leu Gly Ile Asn Asn Thr Ile Met Tyr Asp Gln Val Lys Lys Ser
305                 310                 315                 320

Trp Ala Lys Gln Ser Val Ala Leu Asp Val Leu Ser Tyr His Ala Thr
                325                 330                 335

Cys Ser Lys Ala Glu Val Asp Lys Phe Lys Ala Ala Asn Ile Pro Leu
            340                 345                 350

Val Ser Glu Leu Ala Ile Asp Ile His Phe Asp Asp Phe Ser Leu
        355                 360                 365

Asp Val Asp Ala Met Ile Thr Ala Ala Leu Arg Met Phe Met Glu Leu
    370                 375                 380

Gly Met Val Gln Lys Phe Lys Ile Asp Tyr Glu Thr Leu Cys Arg Trp
385                 390                 395                 400

Leu Leu Thr Val Arg Lys Asn Tyr Arg Met Val Leu Tyr His Asn Trp
                405                 410                 415

Arg His Ala Phe Asn Val Cys Gln Leu Met Phe Ala Met Leu Thr Thr
            420                 425                 430

Ala Gly Phe Gln Glu Ile Leu Thr Glu Val Glu Ile Leu Ala Val Ile
        435                 440                 445

Val Gly Cys Leu Cys His Asp Leu Asp His Arg Gly Thr Asn Asn Ala
    450                 455                 460

Phe Gln Ala Lys Ser Asp Ser Ala Leu Ala Gln Leu Tyr Gly Thr Ser
465                 470                 475                 480

Ala Thr Leu Glu His His His Phe Asn His Ala Val Met Ile Leu Gln
                485                 490                 495

Ser Glu Gly His Asn Ile Phe Ala Asn Leu Ser Ser Lys Glu Tyr Ser
            500                 505                 510

Asp Leu Met Gln Leu Leu Lys Gln Ser Ile Leu Ala Thr Asp Leu Thr
        515                 520                 525

Leu Tyr Phe Glu Arg Arg Thr Glu Phe Phe Glu Leu Val Ser Lys Gly
    530                 535                 540

Ala Tyr Asp Trp Ser Ile Thr Ser His Arg Asp Val Phe Arg Ser Met
545                 550                 555                 560

Leu Met Thr Ala Cys Asp Leu Gly Ala Val Thr Lys Pro Trp Glu Ile
                565                 570                 575

Ser Arg Gln Val Ala Glu Leu Val Thr Ser Glu Phe Phe Glu Gln Gly
            580                 585                 590

Asp Arg Glu Arg Ser Glu Leu Lys Leu Thr Pro Ser Ala Ile Phe Asp
        595                 600                 605
```

-continued

```
Arg Asn Arg Lys Asp Glu Leu Pro Arg Leu Gln Leu Glu Trp Ile Asp
    610                 615                 620

Ser Ile Cys Met Pro Leu Tyr Gln Ala Leu Val Lys Val Asn Ala Lys
625                 630                 635                 640

Leu Lys Pro Met Leu Asp Ser Val Ala Ala Asn Arg Arg Lys Trp Glu
                645                 650                 655

Glu Leu His Gln Lys Arg Leu Gln Val Ser Ala Ala Ser Pro Val Pro
            660                 665                 670

Ser Ser Pro Ser Pro Ala Val Ala Gly Glu Asp Arg Leu
        675                 680                 685

<210> SEQ ID NO 7
<211> LENGTH: 17
<212> TYPE: DNA
<213> ORGANISM: Artificial Sequence
<220> FEATURE:
<223> OTHER INFORMATION: Artificially Synthesized Primer Sequence

<400> SEQUENCE: 7
caygaystgg aycayag                                                   17

<210> SEQ ID NO 8
<211> LENGTH: 17
<212> TYPE: DNA
<213> ORGANISM: Artificial Sequence
<220> FEATURE:
<223> OTHER INFORMATION: Artificially Synthesized Primer Sequence

<400> SEQUENCE: 8
cakgtcwgtk gcyaaka                                                   17

<210> SEQ ID NO 9
<211> LENGTH: 15
<212> TYPE: DNA
<213> ORGANISM: Artificial Sequence
<220> FEATURE:
<223> OTHER INFORMATION: Artificially Synthesized Primer Sequence

<400> SEQUENCE: 9
ctgcttcaaa agctg                                                     15

<210> SEQ ID NO 10
<211> LENGTH: 24
<212> TYPE: DNA
<213> ORGANISM: Artificial Sequence
<220> FEATURE:
<223> OTHER INFORMATION: Artificially Synthesized Primer Sequence

<400> SEQUENCE: 10
atgatccttc aaagtgaggg tcac                                           24

<210> SEQ ID NO 11
<211> LENGTH: 24
<212> TYPE: DNA
<213> ORGANISM: Artificial Sequence
<220> FEATURE:
<223> OTHER INFORMATION: Artificially Synthesized Primer Sequence

<400> SEQUENCE: 11
ggtagcagag gttccataga gttg                                           24

<210> SEQ ID NO 12
<211> LENGTH: 24
<212> TYPE: DNA
```

```
<213> ORGANISM: Artificial Sequence
<220> FEATURE:
<223> OTHER INFORMATION: Artificially Synthesized Primer Sequence

<400> SEQUENCE: 12
ggtcacaata tctttgctaa cctg                                              24

<210> SEQ ID NO 13
<211> LENGTH: 24
<212> TYPE: DNA
<213> ORGANISM: Artificial Sequence
<220> FEATURE:
<223> OTHER INFORMATION: Artificially Synthesized Primer Sequence

<400> SEQUENCE: 13
cttagcttgg aaggcattgt tggt                                              24

<210> SEQ ID NO 14
<211> LENGTH: 24
<212> TYPE: DNA
<213> ORGANISM: Artificial Sequence
<220> FEATURE:
<223> OTHER INFORMATION: Artificially Synthesized Primer Sequence

<400> SEQUENCE: 14
tctgacacca gagggatgtt ggct                                              24

<210> SEQ ID NO 15
<211> LENGTH: 24
<212> TYPE: DNA
<213> ORGANISM: Artificial Sequence
<220> FEATURE:
<223> OTHER INFORMATION: Artificially Synthesized Primer Sequence

<400> SEQUENCE: 15
gtcagtctgt tcttcaaaga ggtc                                              24

<210> SEQ ID NO 16
<211> LENGTH: 24
<212> TYPE: DNA
<213> ORGANISM: Artificial Sequence
<220> FEATURE:
<223> OTHER INFORMATION: Artificially Synthesized Primer Sequence

<400> SEQUENCE: 16
accaacaatg ccttccaagc taag                                              24

<210> SEQ ID NO 17
<211> LENGTH: 24
<212> TYPE: DNA
<213> ORGANISM: Artificial Sequence
<220> FEATURE:
<223> OTHER INFORMATION: Artificially Synthesized Primer Sequence

<400> SEQUENCE: 17
ttccaagcta agagtggctc tgcc                                              24

<210> SEQ ID NO 18
<211> LENGTH: 25
<212> TYPE: DNA
<213> ORGANISM: Artificial Sequence
<220> FEATURE:
<223> OTHER INFORMATION: Artificially Synthesized Primer Sequence

<400> SEQUENCE: 18
tggcgctgaa ctgggaatac tggtg                                             25
```

```
<210> SEQ ID NO 19
<211> LENGTH: 23
<212> TYPE: DNA
<213> ORGANISM: Artificial Sequence
<220> FEATURE:
<223> OTHER INFORMATION: Artificially Synthesized Primer Sequence

<400> SEQUENCE: 19
tcaggctgta gtcatttgc agc                                              23

<210> SEQ ID NO 20
<211> LENGTH: 24
<212> TYPE: DNA
<213> ORGANISM: Artificial Sequence
<220> FEATURE:
<223> OTHER INFORMATION: Artificially Synthesized Primer Sequence

<400> SEQUENCE: 20
tgaggcagca aagagctgag cgtt                                            24

<210> SEQ ID NO 21
<211> LENGTH: 24
<212> TYPE: DNA
<213> ORGANISM: Artificial Sequence
<220> FEATURE:
<223> OTHER INFORMATION: Artificially Synthesized Primer Sequence

<400> SEQUENCE: 21
agcgttagat atggcgattc caca                                            24

<210> SEQ ID NO 22
<211> LENGTH: 24
<212> TYPE: DNA
<213> ORGANISM: Artificial Sequence
<220> FEATURE:
<223> OTHER INFORMATION: Artificially Synthesized Primer Sequence

<400> SEQUENCE: 22
tgtcttgtat ccagttagct tgtc                                            24

<210> SEQ ID NO 23
<211> LENGTH: 18
<212> TYPE: DNA
<213> ORGANISM: Artificial Sequence
<220> FEATURE:
<223> OTHER INFORMATION: Artificially Synthesized Primer Sequence

<400> SEQUENCE: 23
gcgcttgcag cccagggc                                                   18

<210> SEQ ID NO 24
<211> LENGTH: 18
<212> TYPE: DNA
<213> ORGANISM: Artificial Sequence
<220> FEATURE:
<223> OTHER INFORMATION: Artificially Synthesized Primer Sequence

<400> SEQUENCE: 24
ggatccatgg cagcctcc                                                   18

<210> SEQ ID NO 25
<211> LENGTH: 23
<212> TYPE: DNA
<213> ORGANISM: Artificial Sequence
<220> FEATURE:
<223> OTHER INFORMATION: Artificially Synthesized Primer Sequence
```

```
<400> SEQUENCE: 25
ccttagctct ttctgagaag ctc                                              23

<210> SEQ ID NO 26
<211> LENGTH: 23
<212> TYPE: DNA
<213> ORGANISM: Artificial Sequence
<220> FEATURE:
<223> OTHER INFORMATION: Artificially Synthesized Primer Sequence

<400> SEQUENCE: 26
ggatccatgc tgaagcaggc aag                                              23

<210> SEQ ID NO 27
<211> LENGTH: 21
<212> TYPE: DNA
<213> ORGANISM: Artificial Sequence
<220> FEATURE:
<223> OTHER INFORMATION: Artificially Synthesized Primer Sequence

<400> SEQUENCE: 27
ttcatcatct tcagtaaatg g                                                21

<210> SEQ ID NO 28
<211> LENGTH: 24
<212> TYPE: DNA
<213> ORGANISM: Artificial Sequence
<220> FEATURE:
<223> OTHER INFORMATION: Artificially Synthesized Primer Sequence

<400> SEQUENCE: 28
ataatgcatc gggcccaaac tctg                                             24

<210> SEQ ID NO 29
<211> LENGTH: 21
<212> TYPE: DNA
<213> ORGANISM: Artificial Sequence
<220> FEATURE:
<223> OTHER INFORMATION: Artificially Synthesized Primer Sequence

<400> SEQUENCE: 29
ctgtctggag atctcccacg g                                                21

<210> SEQ ID NO 30
<211> LENGTH: 24
<212> TYPE: DNA
<213> ORGANISM: Artificial Sequence
<220> FEATURE:
<223> OTHER INFORMATION: Artificially Synthesized Primer Sequence

<400> SEQUENCE: 30
gtcgacttca gccttggaac acgt                                             24

<210> SEQ ID NO 31
<211> LENGTH: 24
<212> TYPE: DNA
<213> ORGANISM: Artificial Sequence
<220> FEATURE:
<223> OTHER INFORMATION: Artificially Synthesized Primer Sequence

<400> SEQUENCE: 31
atcgctgaca ttcacaggaa ggcc                                             24

<210> SEQ ID NO 32
<211> LENGTH: 21
<212> TYPE: DNA
```

```
<213> ORGANISM: Artificial Sequence
<220> FEATURE:
<223> OTHER INFORMATION: Artificially Synthesized Primer Sequence

<400> SEQUENCE: 32
attgaccacc tccagcaagg c                                              21

<210> SEQ ID NO 33
<211> LENGTH: 21
<212> TYPE: DNA
<213> ORGANISM: Artificial Sequence
<220> FEATURE:
<223> OTHER INFORMATION: Artificially Synthesized Primer Sequence

<400> SEQUENCE: 33
agcattagat atggcgatgc c                                              21

<210> SEQ ID NO 34
<211> LENGTH: 21
<212> TYPE: DNA
<213> ORGANISM: Artificial Sequence
<220> FEATURE:
<223> OTHER INFORMATION: Artificially Synthesized Primer Sequence

<400> SEQUENCE: 34
tcgatcaatg ttaatgacag c                                              21

<210> SEQ ID NO 35
<211> LENGTH: 21
<212> TYPE: DNA
<213> ORGANISM: Artificial Sequence
<220> FEATURE:
<223> OTHER INFORMATION: Artificially Synthesized Primer Sequence

<400> SEQUENCE: 35
tgtgaccttg gagccgtgac c                                              21

<210> SEQ ID NO 36
<211> LENGTH: 24
<212> TYPE: DNA
<213> ORGANISM: Artificial Sequence
<220> FEATURE:
<223> OTHER INFORMATION: Artificially Synthesized Primer Sequence

<400> SEQUENCE: 36
atcttggcct cactgcatca gtgg                                           24

<210> SEQ ID NO 37
<211> LENGTH: 24
<212> TYPE: DNA
<213> ORGANISM: Artificial Sequence
<220> FEATURE:
<223> OTHER INFORMATION: Artificially Synthesized Primer Sequence

<400> SEQUENCE: 37
agcagatagt tcaggatgca gagg                                           24

<210> SEQ ID NO 38
<211> LENGTH: 4170
<212> TYPE: DNA
<213> ORGANISM: Rat
<220> FEATURE:
<221> NAME/KEY: CDS
<222> LOCATION: (169)..(2973)

<400> SEQUENCE: 38
caatcgggat cctgctgttc ctttcaacct ccggttggct ggtggggagg tagtaccgag     60
```

```
ctggggacac gggtgtgggc aaacatgtgc agcaacaact agaggcctca ggacaggtta      120
acgtgtgggt cccagagtag agaggcgaag caaggggtgc ccgggacc atg gca gcc      177
                                                     Met Ala Ala
                                                      1 tcc cgc ctg gac ttc ggg gag gtg gaa act ttc ctg gat agg cac cca      225
Ser Arg Leu Asp Phe Gly Glu Val Glu Thr Phe Leu Asp Arg His Pro
 5              10                  15 gaa ttg ttt gaa gat tac ttg atg cga aaa gga aag cag gag ctg gtg      273
Glu Leu Phe Glu Asp Tyr Leu Met Arg Lys Gly Lys Gln Glu Leu Val
 20              25                  30                  35 gac aag tgg cta caa agg cac agt tcg gga cag ggg gct tca gac ctg      321
Asp Lys Trp Leu Gln Arg His Ser Ser Gly Gln Gly Ala Ser Asp Leu
             40                  45                  50 agg cct gcc ctg gct ggc gct agc agc ttg gct cag agc agt gcc aga      369
Arg Pro Ala Leu Ala Gly Ala Ser Ser Leu Ala Gln Ser Ser Ala Arg
             55                  60                  65 ggc agc act ggc ata ggt ggt ggt gct gga ccc cag ggt tct gcc aac      417
Gly Ser Thr Gly Ile Gly Gly Gly Ala Gly Pro Gln Gly Ser Ala Asn
             70                  75                  80 agt cat ccc gcg tcc ggt ggt ggg gaa agt gcc ggg gtt cct ctg agt      465
Ser His Pro Ala Ser Gly Gly Gly Glu Ser Ala Gly Val Pro Leu Ser
 85                  90                  95 ccc agt tgg gcc agt ggc agc cgg ggc gat ggc aac ctt cag agg aga      513
Pro Ser Trp Ala Ser Gly Ser Arg Gly Asp Gly Asn Leu Gln Arg Arg
100                 105                 110                 115 gct tcg cag aaa gag ctg aga aag agc ttt gcc cgc tcc aaa gcc atc      561
Ala Ser Gln Lys Glu Leu Arg Lys Ser Phe Ala Arg Ser Lys Ala Ile
                120                 125                 130 cat gtg aac agg acc tac gac gaa cag gtg acc tcc cgg gcc cag gag      609
His Val Asn Arg Thr Tyr Asp Glu Gln Val Thr Ser Arg Ala Gln Glu
                135                 140                 145 ccc ctg agc agt gtc cgg agg cga gcc ctg ctc aga aag gcc agc tct      657
Pro Leu Ser Ser Val Arg Arg Arg Ala Leu Leu Arg Lys Ala Ser Ser
150                 155                 160 ctg ccc ccc acc aca gcc cac att ctc agt gcc ctg ctg gaa tcg agg      705
Leu Pro Pro Thr Thr Ala His Ile Leu Ser Ala Leu Leu Glu Ser Arg
165                 170                 175 gtg aat ctt cct cag tat ccc cct acg gcc atc gac tac aaa tgc cac      753
Val Asn Leu Pro Gln Tyr Pro Pro Thr Ala Ile Asp Tyr Lys Cys His
180                 185                 190                 195 ctc aaa aag cat aat gag cga cag ttt ttc ctg gaa ctg gtc aag gac      801
Leu Lys Lys His Asn Glu Arg Gln Phe Phe Leu Glu Leu Val Lys Asp
                200                 205                 210 atc tcc aat gac ctt gac ctc acc agc cta agc tac aag atc ctc atc      849
Ile Ser Asn Asp Leu Asp Leu Thr Ser Leu Ser Tyr Lys Ile Leu Ile
                215                 220                 225 ttt gtc tgt ctc atg gtg gac gct gac cgc tgc tct ctc ttc tta gtg      897
Phe Val Cys Leu Met Val Asp Ala Asp Arg Cys Ser Leu Phe Leu Val
                230                 235                 240 gaa ggg gca gct gct ggt aag aag act ttg gtc tcc aag ttt ttt gac      945
Glu Gly Ala Ala Ala Gly Lys Lys Thr Leu Val Ser Lys Phe Phe Asp
245                 250                 255 gtg cat gca gga acc cca ctg ctg ccc tgc agc acc aca gag aac tca      993
Val His Ala Gly Thr Pro Leu Leu Pro Cys Ser Thr Thr Glu Asn Ser
260                 265                 270                 275 aat gag gtg cag gtc ccc tgg ggc aaa ggt atc att ggc tat gtc ggg     1041
Asn Glu Val Gln Val Pro Trp Gly Lys Gly Ile Ile Gly Tyr Val Gly
                280                 285                 290 gaa cac gga gaa aca gtc aac att ccc gat gcc tac cag gac cga aga     1089
Glu His Gly Glu Thr Val Asn Ile Pro Asp Ala Tyr Gln Asp Arg Arg
```

```
                                                        -continued

Glu His Gly Glu Thr Val Asn Ile Pro Asp Ala Tyr Gln Asp Arg Arg
            295                 300                 305 ttc aat gat gaa att gac aag ctg act gga tac aag aca aaa tca cta    1137
Phe Asn Asp Glu Ile Asp Lys Leu Thr Gly Tyr Lys Thr Lys Ser Leu
310                 315                 320 ttg tgc atg cct atc cgg aac agt gac ggt gag att atc ggt gtg gcc    1185
Leu Cys Met Pro Ile Arg Asn Ser Asp Gly Glu Ile Ile Gly Val Ala
    325                 330                 335 cag gcg ata aat aag gtt cct gag ggt gct cca ttt aca gaa gac gac    1233
Gln Ala Ile Asn Lys Val Pro Glu Gly Ala Pro Phe Thr Glu Asp Asp
340                 345                 350                 355 gaa aaa gtt atg cag atg tat ctt cca ttc tgt ggc atc gcc ata tct    1281
Glu Lys Val Met Gln Met Tyr Leu Pro Phe Cys Gly Ile Ala Ile Ser
                360                 365                 370 aat gct cag ctc ttc gcc gcc tcg agg aaa gaa tat gaa aga agt agg    1329
Asn Ala Gln Leu Phe Ala Ala Ser Arg Lys Glu Tyr Glu Arg Ser Arg
        375                 380                 385 gcc ttg ctg gag gtg gtc aat gac ctc ttt gaa gaa cag act gac ctg    1377
Ala Leu Leu Glu Val Val Asn Asp Leu Phe Glu Glu Gln Thr Asp Leu
            390                 395                 400 gaa aag att gtc aag aaa ata atg cat cgg gcc caa act ctg ttg aaa    1425
Glu Lys Ile Val Lys Lys Ile Met His Arg Ala Gln Thr Leu Leu Lys
405                 410                 415 tgt gaa cgc tgt tcc gtt tta ctt cta gaa gac att gaa tca cca gtg    1473
Cys Glu Arg Cys Ser Val Leu Leu Leu Glu Asp Ile Glu Ser Pro Val
420                 425                 430                 435 gtg aag ttt acc aaa tcc ttt gaa ctg atg tcc cca aag tgc agt gcg    1521
Val Lys Phe Thr Lys Ser Phe Glu Leu Met Ser Pro Lys Cys Ser Ala
        440                 445                 450 gac gcg gag aac agt ttc aaa gaa agt gtg gag aag tca tct tac tcc    1569
Asp Ala Glu Asn Ser Phe Lys Glu Ser Val Glu Lys Ser Ser Tyr Ser
            455                 460                 465 gac tgg ctg ata aat aac agt atc gct gag ctg gtt gct tcg aca ggc    1617
Asp Trp Leu Ile Asn Asn Ser Ile Ala Glu Leu Val Ala Ser Thr Gly
        470                 475                 480 ctt cct gtg aat gtc agc gat gcc tac cag gac cca cgc ttt gac gct    1665
Leu Pro Val Asn Val Ser Asp Ala Tyr Gln Asp Pro Arg Phe Asp Ala
485                 490                 495 gag gct gac cag ata tct ggc ttt cat ata aga tct gtt ctc tgt gtc    1713
Glu Ala Asp Gln Ile Ser Gly Phe His Ile Arg Ser Val Leu Cys Val
500                 505                 510                 515 cct att tgg aac agc aac cac caa ata ata ggg gtc gct caa gtg ctg    1761
Pro Ile Trp Asn Ser Asn His Gln Ile Ile Gly Val Ala Gln Val Leu
        520                 525                 530 aac aga ctc gat ggg aaa cct ttt gat gat gct gac caa agg ctt ttt    1809
Asn Arg Leu Asp Gly Lys Pro Phe Asp Asp Ala Asp Gln Arg Leu Phe
            535                 540                 545 gag gcc ttt gtc atc ttt tgt ggc ctt ggt att aac aac acg att atg    1857
Glu Ala Phe Val Ile Phe Cys Gly Leu Gly Ile Asn Asn Thr Ile Met
        550                 555                 560 tat gac caa gtg aag aag tcc tgg gcc aag cag tcc gtg gct ctt gat    1905
Tyr Asp Gln Val Lys Lys Ser Trp Ala Lys Gln Ser Val Ala Leu Asp
565                 570                 575 gtg ctg tcc tac cac gcc acg tgt tcc aag gct gaa gtt gac aag ttt    1953
Val Leu Ser Tyr His Ala Thr Cys Ser Lys Ala Glu Val Asp Lys Phe
580                 585                 590                 595 aag gca gcc aac atc ccc ctg gtg tcg gaa ctg gcc atc gat gac atc    2001
Lys Ala Ala Asn Ile Pro Leu Val Ser Glu Leu Ala Ile Asp Asp Ile
        600                 605                 610 cat ttt gat gac ttt tcc ctt gat gtt gat gcc atg atc aca gcc gct    2049
His Phe Asp Asp Phe Ser Leu Asp Val Asp Ala Met Ile Thr Ala Ala
```

-continued

| | | | | | | | | | | | | | | | |
|---|---|---|---|---|---|---|---|---|---|---|---|---|---|---|---|
| His | Phe | Asp | Asp | Phe | Ser | Leu | Asp | Val | Asp | Ala | Met | Ile | Thr | Ala | Ala |
| | | | 615 | | | | 620 | | | | | 625 | | | |

| cta | cgg | atg | ttc | atg | gag | ctg | ggg | atg | gta | cag | aaa | ttt | aaa | atc | gac | 2097 |
|---|---|---|---|---|---|---|---|---|---|---|---|---|---|---|---|---|
| Leu | Arg | Met | Phe | Met | Glu | Leu | Gly | Met | Val | Gln | Lys | Phe | Lys | Ile | Asp | |
| | 630 | | | | | 635 | | | | | 640 | | | | | |

| tat | gag | acc | ctg | tgc | agg | tgg | ctt | ctg | aca | gta | agg | aaa | aac | tat | cgg | 2145 |
|---|---|---|---|---|---|---|---|---|---|---|---|---|---|---|---|---|
| Tyr | Glu | Thr | Leu | Cys | Arg | Trp | Leu | Leu | Thr | Val | Arg | Lys | Asn | Tyr | Arg | |
| 645 | | | | | 650 | | | | | 655 | | | | | | |

| atg | gtt | ctc | tac | cac | aac | tgg | aga | cat | gcc | ttc | aac | gtg | tgc | cag | ctg | 2193 |
|---|---|---|---|---|---|---|---|---|---|---|---|---|---|---|---|---|
| Met | Val | Leu | Tyr | His | Asn | Trp | Arg | His | Ala | Phe | Asn | Val | Cys | Gln | Leu | |
| 660 | | | | 665 | | | | | 670 | | | | | 675 | | |

| atg | ttt | gcc | atg | cta | act | act | gct | ggg | ttt | caa | gag | att | ctg | acc | gag | 2241 |
|---|---|---|---|---|---|---|---|---|---|---|---|---|---|---|---|---|
| Met | Phe | Ala | Met | Leu | Thr | Thr | Ala | Gly | Phe | Gln | Glu | Ile | Leu | Thr | Glu | |
| | | | 680 | | | | | 685 | | | | | 690 | | | |

| gtg | gaa | att | tta | gcg | gtg | att | gtg | gga | tgc | ctg | tgt | cat | gac | ctc | gac | 2289 |
|---|---|---|---|---|---|---|---|---|---|---|---|---|---|---|---|---|
| Val | Glu | Ile | Leu | Ala | Val | Ile | Val | Gly | Cys | Leu | Cys | His | Asp | Leu | Asp | |
| | | 695 | | | | | 700 | | | | | 705 | | | | |

| cac | agg | gga | acc | aac | aat | gcc | ttc | caa | gct | aag | agt | gac | tct | gca | ctg | 2337 |
|---|---|---|---|---|---|---|---|---|---|---|---|---|---|---|---|---|
| His | Arg | Gly | Thr | Asn | Asn | Ala | Phe | Gln | Ala | Lys | Ser | Asp | Ser | Ala | Leu | |
| 710 | | | | | 715 | | | | | 720 | | | | | | |

| gcc | cag | ctc | tat | ggg | acc | tca | gcg | acc | tta | gag | cat | cac | cac | ttt | aac | 2385 |
|---|---|---|---|---|---|---|---|---|---|---|---|---|---|---|---|---|
| Ala | Gln | Leu | Tyr | Gly | Thr | Ser | Ala | Thr | Leu | Glu | His | His | His | Phe | Asn | |
| | 725 | | | | | 730 | | | | | 735 | | | | | |

| cac | gcc | gtg | atg | atc | ctt | cag | agt | gag | ggt | cac | aac | atc | ttt | gct | aat | 2433 |
|---|---|---|---|---|---|---|---|---|---|---|---|---|---|---|---|---|
| His | Ala | Val | Met | Ile | Leu | Gln | Ser | Glu | Gly | His | Asn | Ile | Phe | Ala | Asn | |
| 740 | | | | | 745 | | | | | 750 | | | | | 755 | |

| ttg | tcc | tcc | aag | gaa | tac | agc | gac | ctc | atg | cag | ctc | ctg | aag | cag | tcg | 2481 |
|---|---|---|---|---|---|---|---|---|---|---|---|---|---|---|---|---|
| Leu | Ser | Ser | Lys | Glu | Tyr | Ser | Asp | Leu | Met | Gln | Leu | Leu | Lys | Gln | Ser | |
| | | | | 760 | | | | | 765 | | | | | 770 | | |

| ata | cta | gcc | act | gac | ctc | acg | ctg | tac | ttc | gag | aga | aga | act | gag | ttc | 2529 |
|---|---|---|---|---|---|---|---|---|---|---|---|---|---|---|---|---|
| Ile | Leu | Ala | Thr | Asp | Leu | Thr | Leu | Tyr | Phe | Glu | Arg | Arg | Thr | Glu | Phe | |
| | | | 775 | | | | | 780 | | | | | 785 | | | |

| ttc | gag | ctt | gtc | agt | aaa | gga | gcc | tat | gat | tgg | agc | atc | aca | agt | cac | 2577 |
|---|---|---|---|---|---|---|---|---|---|---|---|---|---|---|---|---|
| Phe | Glu | Leu | Val | Ser | Lys | Gly | Ala | Tyr | Asp | Trp | Ser | Ile | Thr | Ser | His | |
| | 790 | | | | | 795 | | | | | 800 | | | | | |

| cgc | gat | gtg | ttt | cga | tca | atg | tta | atg | aca | gct | tgt | gac | ctt | gga | gcc | 2625 |
|---|---|---|---|---|---|---|---|---|---|---|---|---|---|---|---|---|
| Arg | Asp | Val | Phe | Arg | Ser | Met | Leu | Met | Thr | Ala | Cys | Asp | Leu | Gly | Ala | |
| 805 | | | | | 810 | | | | | 815 | | | | | | |

| gtg | acc | aaa | ccg | tgg | gag | atc | tcc | aga | cag | gtg | gct | gaa | ctt | gtc | acc | 2673 |
|---|---|---|---|---|---|---|---|---|---|---|---|---|---|---|---|---|
| Val | Thr | Lys | Pro | Trp | Glu | Ile | Ser | Arg | Gln | Val | Ala | Glu | Leu | Val | Thr | |
| 820 | | | | 825 | | | | | 830 | | | | | 835 | | |

| agc | gag | ttc | ttc | gaa | caa | gga | gat | cgg | gag | agg | tcg | gaa | ctc | aag | ctc | 2721 |
|---|---|---|---|---|---|---|---|---|---|---|---|---|---|---|---|---|
| Ser | Glu | Phe | Phe | Glu | Gln | Gly | Asp | Arg | Glu | Arg | Ser | Glu | Leu | Lys | Leu | |
| | | | 840 | | | | | 845 | | | | | 850 | | | |

| acc | ccc | tct | gct | att | ttt | gac | cgg | aac | cgg | aaa | gat | gag | ctg | cct | cgg | 2769 |
|---|---|---|---|---|---|---|---|---|---|---|---|---|---|---|---|---|
| Thr | Pro | Ser | Ala | Ile | Phe | Asp | Arg | Asn | Arg | Lys | Asp | Glu | Leu | Pro | Arg | |
| | | | 855 | | | | | 860 | | | | | 865 | | | |

| ctg | caa | ctg | gag | tgg | att | gac | agc | atc | tgc | atg | cct | ttg | tat | cag | gcc | 2817 |
|---|---|---|---|---|---|---|---|---|---|---|---|---|---|---|---|---|
| Leu | Gln | Leu | Glu | Trp | Ile | Asp | Ser | Ile | Cys | Met | Pro | Leu | Tyr | Gln | Ala | |
| | 870 | | | | | 875 | | | | | 880 | | | | | |

| ttg | gtg | aaa | gtc | aat | gca | aaa | ctg | aag | ccg | atg | ctg | gac | tca | gtg | gcc | 2865 |
|---|---|---|---|---|---|---|---|---|---|---|---|---|---|---|---|---|
| Leu | Val | Lys | Val | Asn | Ala | Lys | Leu | Lys | Pro | Met | Leu | Asp | Ser | Val | Ala | |
| 885 | | | | | 890 | | | | | 895 | | | | | | |

| gcc | aac | cgc | agg | aag | tgg | gaa | gag | ttg | cac | caa | aaa | aga | cta | cag | gtc | 2913 |
|---|---|---|---|---|---|---|---|---|---|---|---|---|---|---|---|---|
| Ala | Asn | Arg | Arg | Lys | Trp | Glu | Glu | Leu | His | Gln | Lys | Arg | Leu | Gln | Val | |
| 900 | | | | 905 | | | | | 910 | | | | | 915 | | |

| tct | gct | gcc | tcc | cca | gtc | cct | tcc | agt | ccc | agc | cca | gcg | gtg | gcc | gga | 2961 |
|---|---|---|---|---|---|---|---|---|---|---|---|---|---|---|---|---|
| Ser | Ala | Ala | Ser | Pro | Val | Pro | Ser | Ser | Pro | Ser | Pro | Ala | Val | Ala | Gly | |
| | | | | 920 | | | | | 925 | | | | | 930 | | |

| gag | gac | aga | ctg | taaaccaccc | agagctgctg | cgccaccctg | tggcctggag | | | | | | | | | 3013 |
|---|---|---|---|---|---|---|---|---|---|---|---|---|---|---|---|---|
| Glu | Asp | Arg | Leu | | | | | | | | | | | | | |

```
Glu Asp Arg Leu
        935 gaccctctgc atcctgaact atctgctttg gttgaatagc atcaccctct tcgttcagct    3073 cggacagtcc taaagctttg actggatcag gaagcacaca aggaagtgtg cttggcggca    3133 gagaaacgga aggatgaaga gaatacgacc ctcaactttg tcatgaaccc atgctgctgg    3193 atttggatcc gtggacctga aggccatcac cccactcgtg ctgagttgag aggacaccgt    3253 tgtaaaagtg tcactatggc tgcttcctgt atggcacttt tctgttatga gcatttcctt    3313 tctgtgcagc ctctccggag caggctccag ccggtcccaa gaatgcagat ttgcattcta    3373 ggtgttttgt ttctaatcta ctgcttcttt gtaatgcacc agacccttcg tctcctttgc    3433 tagtggataa gcctgctccc tttattagag ccaggtaacc ccaatcttgc ttgccacagt    3493 agtaatatag tgtgtttgtc taattggtgt tacacaggag ctgtaactct gcagtgagat    3553 agatcatggt tcagcttttt aattcagcct ttgttgcaaa caaagccttt ttctaggggg    3613 aaacagatta ataattttat taaagcaaag gtgaaaagga atctaaggcc acatgtacaa    3673 gtgacatgta tgaacaccag aaatgcttcc aacaaagaaa tatttcacag gtgcagagga    3733 accctgtgac cagtcgtgga atagtttgag gtgaagggga tgaaggtttg gggataaaat    3793 ttaaggaacc ctgattttac attttttcctt acatgtaaaa aagaatgttc tagaaaggcc    3853 aggaaataac acctgcacaa cctatatcca gtaagaagtc agatctacag cacgtgaaaa    3913 cagtttaaaa gaggtatgct cactagaaag ctgcctgaga cactaaggac aggatctgtc    3973 ttacccaaag aacattgggc ttcctgtccc tcactttgca ttactagttg agtgagtttg    4033 gacctagatt tctctgtgtc aagcgagatt acactaggaa tttatttgca gtaatcttag    4093 cattaaaatc ttttgtccaa ataaacttcc aaggattccc cagggcacaa ggaaaaaaaa    4153 aaaaaaaaaa aaaaaaa                                                    4170

<210> SEQ ID NO 39
<211> LENGTH: 935
<212> TYPE: PRT
<213> ORGANISM: Rat

<400> SEQUENCE: 39

Met Ala Ala Ser Arg Leu Asp Phe Gly Glu Val Glu Thr Phe Leu Asp
1               5                   10                  15

Arg His Pro Glu Leu Phe Glu Asp Tyr Leu Met Arg Lys Gly Lys Gln
            20                  25                  30

Glu Leu Val Asp Lys Trp Leu Gln Arg His Ser Ser Gly Gln Gly Ala
        35                  40                  45

Ser Asp Leu Arg Pro Ala Leu Ala Gly Ala Ser Leu Ala Gln Ser
    50                  55                  60

Ser Ala Arg Gly Ser Thr Gly Ile Gly Gly Ala Gly Pro Gln Gly
65                  70                  75                  80

Ser Ala Asn Ser His Pro Ala Ser Gly Gly Glu Ser Ala Gly Val
                85                  90                  95

Pro Leu Ser Pro Ser Trp Ala Ser Gly Ser Arg Gly Asp Gly Asn Leu
            100                 105                 110

Gln Arg Arg Ala Ser Gln Lys Glu Leu Arg Lys Ser Phe Ala Arg Ser
        115                 120                 125

Lys Ala Ile His Val Asn Arg Thr Tyr Asp Glu Gln Val Thr Ser Arg
    130                 135                 140

Ala Gln Glu Pro Leu Ser Ser Val Arg Arg Arg Ala Leu Leu Arg Lys
145                 150                 155                 160
```

```
Ala Ser Ser Leu Pro Pro Thr Thr Ala His Ile Leu Ser Ala Leu Leu
                165                 170                 175

Glu Ser Arg Val Asn Leu Pro Gln Tyr Pro Thr Ala Ile Asp Tyr
            180                 185                 190

Lys Cys His Leu Lys Lys His Asn Glu Arg Gln Phe Phe Leu Glu Leu
            195                 200                 205

Val Lys Asp Ile Ser Asn Asp Leu Asp Leu Thr Ser Leu Ser Tyr Lys
    210                 215                 220

Ile Leu Ile Phe Val Cys Leu Met Val Asp Ala Asp Arg Cys Ser Leu
225                 230                 235                 240

Phe Leu Val Glu Gly Ala Ala Gly Lys Lys Thr Leu Val Ser Lys
                245                 250                 255

Phe Phe Asp Val His Ala Gly Thr Pro Leu Leu Pro Cys Ser Thr Thr
            260                 265                 270

Glu Asn Ser Asn Glu Val Gln Val Pro Trp Gly Lys Gly Ile Ile Gly
            275                 280                 285

Tyr Val Gly Glu His Gly Glu Thr Val Asn Ile Pro Asp Ala Tyr Gln
    290                 295                 300

Asp Arg Arg Phe Asn Asp Glu Ile Asp Lys Leu Thr Gly Tyr Lys Thr
305                 310                 315                 320

Lys Ser Leu Leu Cys Met Pro Ile Arg Asn Ser Asp Gly Glu Ile Ile
                325                 330                 335

Gly Val Ala Gln Ala Ile Asn Lys Val Pro Glu Gly Ala Pro Phe Thr
            340                 345                 350

Glu Asp Asp Glu Lys Val Met Gln Met Tyr Leu Pro Phe Cys Gly Ile
            355                 360                 365

Ala Ile Ser Asn Ala Gln Leu Phe Ala Ala Ser Arg Lys Glu Tyr Glu
    370                 375                 380

Arg Ser Arg Ala Leu Leu Glu Val Val Asn Asp Leu Phe Glu Glu Gln
385                 390                 395                 400

Thr Asp Leu Glu Lys Ile Val Lys Lys Ile Met His Arg Ala Gln Thr
                405                 410                 415

Leu Leu Lys Cys Glu Arg Cys Ser Val Leu Leu Leu Glu Asp Ile Glu
            420                 425                 430

Ser Pro Val Val Lys Phe Thr Lys Ser Phe Glu Leu Met Ser Pro Lys
            435                 440                 445

Cys Ser Ala Asp Ala Glu Asn Ser Phe Lys Glu Ser Val Glu Lys Ser
    450                 455                 460

Ser Tyr Ser Asp Trp Leu Ile Asn Asn Ser Ile Ala Glu Leu Val Ala
465                 470                 475                 480

Ser Thr Gly Leu Pro Val Asn Val Ser Asp Ala Tyr Gln Asp Pro Arg
                485                 490                 495

Phe Asp Ala Glu Ala Asp Gln Ile Ser Gly Phe His Ile Arg Ser Val
            500                 505                 510

Leu Cys Val Pro Ile Trp Asn Ser Asn His Gln Ile Ile Gly Val Ala
            515                 520                 525

Gln Val Leu Asn Arg Leu Asp Gly Lys Pro Phe Asp Asp Ala Asp Gln
    530                 535                 540

Arg Leu Phe Glu Ala Phe Val Ile Phe Cys Gly Leu Gly Ile Asn Asn
545                 550                 555                 560

Thr Ile Met Tyr Asp Gln Val Lys Lys Ser Trp Ala Lys Gln Ser Val
                565                 570                 575

Ala Leu Asp Val Leu Ser Tyr His Ala Thr Cys Ser Lys Ala Glu Val
```

```
                    580                 585                 590
Asp Lys Phe Lys Ala Ala Asn Ile Pro Leu Val Ser Glu Leu Ala Ile
                595                 600                 605

Asp Asp Ile His Phe Asp Asp Phe Ser Leu Asp Val Asp Ala Met Ile
610                 615                 620

Thr Ala Ala Leu Arg Met Phe Met Glu Leu Gly Met Val Gln Lys Phe
625                 630                 635                 640

Lys Ile Asp Tyr Glu Thr Leu Cys Arg Trp Leu Leu Thr Val Arg Lys
                645                 650                 655

Asn Tyr Arg Met Val Leu Tyr His Asn Trp Arg His Ala Phe Asn Val
                660                 665                 670

Cys Gln Leu Met Phe Ala Met Leu Thr Thr Ala Gly Phe Gln Glu Ile
                675                 680                 685

Leu Thr Glu Val Glu Ile Leu Ala Val Ile Val Gly Cys Leu Cys His
                690                 695                 700

Asp Leu Asp His Arg Gly Thr Asn Asn Ala Phe Gln Ala Lys Ser Asp
705                 710                 715                 720

Ser Ala Leu Ala Gln Leu Tyr Gly Thr Ser Ala Thr Leu Glu His His
                725                 730                 735

His Phe Asn His Ala Val Met Ile Leu Gln Ser Glu Gly His Asn Ile
                740                 745                 750

Phe Ala Asn Leu Ser Ser Lys Glu Tyr Ser Asp Leu Met Gln Leu Leu
                755                 760                 765

Lys Gln Ser Ile Leu Ala Thr Asp Leu Thr Leu Tyr Phe Glu Arg Arg
                770                 775                 780

Thr Glu Phe Phe Glu Leu Val Ser Lys Gly Ala Tyr Asp Trp Ser Ile
785                 790                 795                 800

Thr Ser His Arg Asp Val Phe Arg Ser Met Leu Met Thr Ala Cys Asp
                805                 810                 815

Leu Gly Ala Val Thr Lys Pro Trp Glu Ile Ser Arg Gln Val Ala Glu
                820                 825                 830

Leu Val Thr Ser Glu Phe Phe Glu Gln Gly Asp Arg Glu Arg Ser Glu
                835                 840                 845

Leu Lys Leu Thr Pro Ser Ala Ile Phe Asp Arg Asn Arg Lys Asp Glu
850                 855                 860

Leu Pro Arg Leu Gln Leu Glu Trp Ile Asp Ser Ile Cys Met Pro Leu
865                 870                 875                 880

Tyr Gln Ala Leu Val Lys Val Asn Ala Lys Leu Lys Pro Met Leu Asp
                885                 890                 895

Ser Val Ala Ala Asn Arg Arg Lys Trp Glu Glu Leu His Gln Lys Arg
                900                 905                 910

Leu Gln Val Ser Ala Ala Ser Pro Val Pro Ser Ser Pro Ser Pro Ala
                915                 920                 925

Val Ala Gly Glu Asp Arg Leu
                930                 935

<210> SEQ ID NO 40
<211> LENGTH: 27
<212> TYPE: DNA
<213> ORGANISM: Artificial Sequence
<220> FEATURE:
<223> OTHER INFORMATION: Artificially Synthesized Primer Sequence

<400> SEQUENCE: 40
cctccggaca ctgctcaggg gctcctg                                           27
```

```
<210> SEQ ID NO 41
<211> LENGTH: 25
<212> TYPE: DNA
<213> ORGANISM: Artificial Sequence
<220> FEATURE:
<223> OTHER INFORMATION: Artificially Synthesized Primer Sequence

<400> SEQUENCE: 41
ggaggtcacc tgttcgtcgt aggtc                                            25

<210> SEQ ID NO 42
<211> LENGTH: 24
<212> TYPE: DNA
<213> ORGANISM: Artificial Sequence
<220> FEATURE:
<223> OTHER INFORMATION: Artificially Synthesized Primer Sequence

<400> SEQUENCE: 42
gtgtgggcaa acatgtgcag caac                                             24
```